United States Patent [19]

Kirkpatrick et al.

[11] 4,292,071
[45] Sep. 29, 1981

[54] ISOTHIOUREIDO ISOINDOLEDIONES AND USE AS PLANT GROWTH REGULATORS

[75] Inventors: Joel L. Kirkpatrick, Washington Crossing, Pa.; Natu R. Patel, Overland Park, Kans.; Jerry L. Rutter, Mentor, Ohio

[73] Assignee: Gulf Oil Corporation, Pittsburgh, Pa.

[21] Appl. No.: 133,888

[22] Filed: Apr. 10, 1980

Related U.S. Application Data

[63] Continuation-in-part of Ser. No. 35,875, May 3, 1979, abandoned.

[51] Int. Cl.³ .................... A01N 43/38; C07D 209/48
[52] U.S. Cl. .......................................... 71/96; 71/73; 71/74; 71/76; 71/90; 71/94; 260/245.7; 260/326 S; 544/54; 546/273; 548/139; 548/191
[58] Field of Search .................... 71/74, 76, 95, 96; 260/326 S, 326 N

[56] References Cited

U.S. PATENT DOCUMENTS

| | | | |
|---|---|---|---|
| 2,661,350 | 12/1953 | Hiltman et al. | 260/326 S |
| 2,872,450 | 2/1959 | Sasse et al. | 260/326 S |
| 3,410,842 | 11/1968 | Allais et al. | 71/95 |
| 3,481,951 | 12/1969 | Boroschewski et al. | 260/326 N |

FOREIGN PATENT DOCUMENTS

| | | |
|---|---|---|
| 1174103 | 9/1962 | Fed. Rep. of Germany . |
| 50-121175 | 9/1975 | Japan . |
| 51-14885 | 5/1976 | Japan . |
| 53-74549 | 7/1978 | Japan . |
| 1272920 | 5/1972 | United Kingdom . |

OTHER PUBLICATIONS

E. Hoggarth, 1949, J. Chem. Soc., 198–223.
Derwent Abstract of W. German Pat. No. 2,126,304.
Derwent Abstract of W. German Pat. No. 2,163,619.
S. Amer., Nucleus (Calcutta) 1973, 16(1), 26–28.
Meran, Gh. Rev. Stiintifica, "V. Adamachi", 32, 136–138 (1946).
N. Buer Hoi et al., Bull Soc. Chim. France, 1956, 363–369.
P. Pel'kis et al., Zh. Obsch. Khim. 31, 3726–3728 (1961).

Primary Examiner—Donald G. Daus
Assistant Examiner—M. C. Eakin
Attorney, Agent, or Firm—Carl A. Cline

[57] ABSTRACT

A novel class of compounds which are useful as plant growth regulators is disclosed, having the general structural formula:

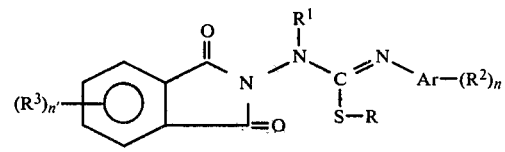

In which R is cyano $C_1$ to $C_5$ alkyl, alkenyl or alkynyl to which may be attached phenyl, halophenyl, methylphenyl, pyridyl, benzoyl, trimethylacetyl, phenoxy, halophenoxy, halobenzoyl, N-phenylcarbamyl, N-alkylcarbamyl, N-trifluoromethylthiadiazolylcarbamyl, carboxy, carbalkoxy or halo substituents, $R^1$ is H, acetyl $C_1$ to $C_3$ alkyl, alkenyl or alkynyl to which may be attached phenyl, halophenyl, carbethoxy, vinyloxy or phenoxy groups, or R and $R^1$ together may be $C_2$ to $C_4$ alkylene, Ar is phenyl or benzoyl, $R^2$ is $C_1$ to $C_4$ alkyl, alkoxy, alkylene, alkylamino or alkylthio; phenoxy, benzyloxy, carbalkoxy, acetyl, methylenedioxy, trifluoromethyl, nitro, halo or cyano and n may be zero or an integer from 1 to 4, with the provision that at least one position ortho to the point of attachment of a phenyl ring of the Ar structure must be unsubstituted, $R^3$ is lower alkyl or halo and n' may be zero or an integer from 1 to 4.

6 Claims, No Drawings

ISOTHIOUREIDO ISOINDOLEDIONES AND USE AS PLANT GROWTH REGULATORS

This application is a continuation-in-part of copending U.S. Ser. No. 035,875, filed May 3, 1979, now abandoned which is incorporated herein by reference.

DESCRIPTION OF THE INVENTION

Growth regulating effects have been observed upon application of many chemical substances to plants. In general, very few of these substances can be used with benefit to the plants which are affected. In most instances the beneficial effects, if any, are minor and the major effects are so drastic that the compounds can only be used for the destruction of the plants. Examples of compounds with drastic effects which have become useful as herbicides are 2,4-D, EPTC and alachlor. Although a relatively small number of growth regulants has proved to be commercially useful, there are many uses for active compounds, among which are the following:

Increase or induce flowering (pineapple).

Increase blossom set, pod set, seed set, and/or fruit set (prevent abortion of flowers or withered blossoms).

Increase size of fruits, vegetables, seed, and/or tubers (grapes, soybeans, sugar beets, etc.)

Decrease size of fruits, vegetables, seed, and/or tubers (potatoes, and grapefruits).

Increase number of tillers (cereals).

Increase number of shoots from crown (alfalfa).

Increase branching (soybeans) or widen branches (apples).

We have now discovered a group of novel compounds which display a great variety of growth regulating effects, indicating utility for many purposes, including uses mentioned above.

Briefly, the novel class of growth regulant compounds has the general structural formula:

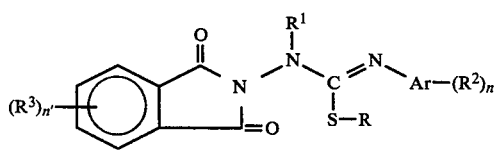

In which R is cyano, $C_1$ to $C_4$ alkyl, $C_3$ to $C_5$ alkenyl or fluoroalkenyl, propynyl, phenylallyl or $C_1$ to $C_3$ alkyl to which is attached a phenyl, bromophenyl, chlorophenyl, methylphenyl, pyridyl, benzoyl, trimethylacetyl, phenoxy, chlorophenoxy, methylthio, fluorobenzoyl, N-phenylcarbamyl, N-ethylcarbamyl, N-trifluoromethylthiadiazolylcarbamyl, carboxy or carbethoxy substituent.

$R^1$ is H, acetyl, $C_1$ to $C_3$ alkyl, alkenyl or alkynyl to which may be attached phenyl, halophenyl, carbethoxy, vinyloxy or phenoxy groups, or R and $R^1$ together may be $C_2$ to $C_4$ alkylene, Ar is phenyl or benzoyl, $R^2$ is $C_1$ to $C_4$ alkyl, alkoxy, alkylene, alkylamino or alkylthio; phenoxy, benzyloxy, carbalkoxy, acetyl, methylenedioxy, trifluoromethyl, nitro, halo or cyano and n may be zero or an integer from 1 to 4, with the provision that at least one position ortho to the point of attachment of a phenyl ring of the Ar structure must be unsubstituted, $R^3$ is lower alkyl or halo and n' may be zero or an integer from 1 to 4.

By virtue of their basic chemical characteristics, the novel compounds may also exist in the form of salts, by addition of a strong acid, such as HBr or HCl. In the salt form the compounds are more easily formulated in water-soluble and water-dispersible formulations.

By selection of the substituent R, the lipophilic properties of the novel compounds may be modified to obtain desirable improvements in ease of formulation, particularly as emulsifiable concentrates, and also improvements in activity on many plant spacies.

The nature of the substituent group $R^1$ is important to the intensity of the growth regulator effect. For highest activity, small alkyl or alkenyl groups having one to three carbon atoms are preferred.

The nature of the $R^2$ substituents is not as critical as the aforementioned groups. However, both activity and selectivity of action may be adjusted to some degree by selection of these groups. In general, $C_1$ to $C_4$ alkyl or alkoxy, halo or cyano substituents are preferred and Ar is preferably phenyl.

In general the substituents designated $R^3$ do not enhance appreciably the activity of the growth regulators. However, by choice of type and position of the $R^3$ substituents, chemical stability may be improved and the growth regulator effect may be prolonged. Prolonging the effect may in some instances eliminate the need for a second application, so that the compounds may be utilized more efficiently. Unless this is economically advantageous, however, compounds in which n'=0 are preferred.

SYNTHESIS OF THE GROWTH REGULANTS

The novel compounds of this invetion may be manufactured by means of the general method comprising reacting a compound of the formula:

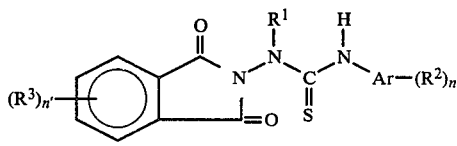

in a non-reactive polar organic solvent with a compound of the formula R—X in which X is a leaving group exemplified by a chlorine, bromine, iodine or sulfate substituent. Specific procedures which are suitable for synthesis of representative compounds are outlined in the following chart and exemplified below.

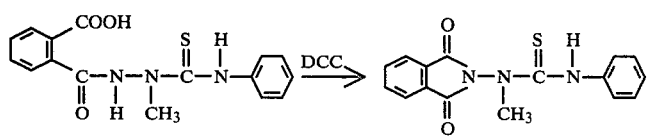

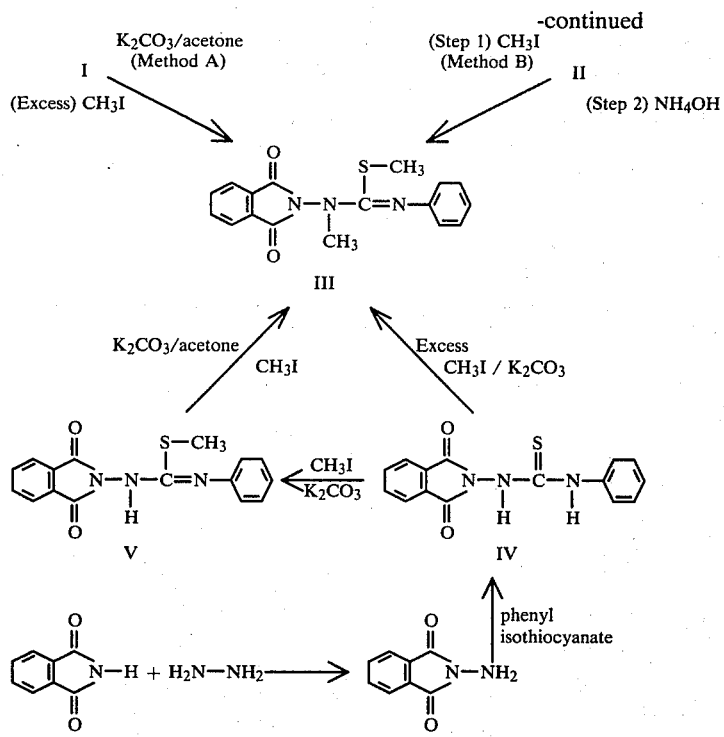

It will be understood that when it is desired that R and $R^1$ shall be different, the alkylation at the sulfur and amino locations is conveniently done in separate reaction steps. The following specific procedures illustrate the general methods of synthesis.

SYNTHESIS OF METHYL HYDROGEN PHTHALATE

Methanol (300 ml) was added in a single portion to 148 g (1.00 mole) of phthalic anhydride and the resulting suspension was stirred and heated at reflux for 36 hours; solution occurred during heating. The solvent was removed and the product was recrystallized from a mixture of ethyl acetate and hexane to afford 114.6 g of the title compound (Lit.: Beilstein, 9,797—mp 82.5°, 84°).

SYNTHESIS OF METHYL PHTHALOYL CHLORIDE

Methyl hydrogen phthalate (110.0 g., 0.611 mole) and thionyl chloride (77.4 g., 0.650 mole) were mixed in 200 ml of chloroform, keeping the temperature below 30°. After stirring for two hours at room temperature, the system was heated at reflux for five hours. The solvent was evaporated at reduced pressure and the crude product (120.9 g) was used without further purification (Lit.: Beilstein, 9, 797—no constants).

SYNTHESIS OF 2-(2-carboxybenzoyl)-1-methyl-N-phenylhydrazinethiocarboxamide (I)

This compound was made by reacting phthalic anhydride with 1-methyl-N-phenylhydrazinethiocarboxamide according to conventional procedures, as follows:

The hydrazinethiocarboxamide was dissolved in about 75 ml of dimethylformamide and placed in a 3-necked round-bottomed flask equipped with magnetic stirrer, condenser, additional powder funnel and thermometer. The anhydride was added in portions at 20°. The contents were stirred overnight at room temperature, then poured into ice water the following morning. The resulting solid was recrystallized in hexane and ethanol (m.p. 155°–156° C.)

Optionally ring substituted phthalic anhydrides and substituted 2-carbomethoxybenzoyl chlorides may be condensed with substituted 1-methylhydrazinethiocarboxamides to give desired intermediate compounds as in the following scheme:

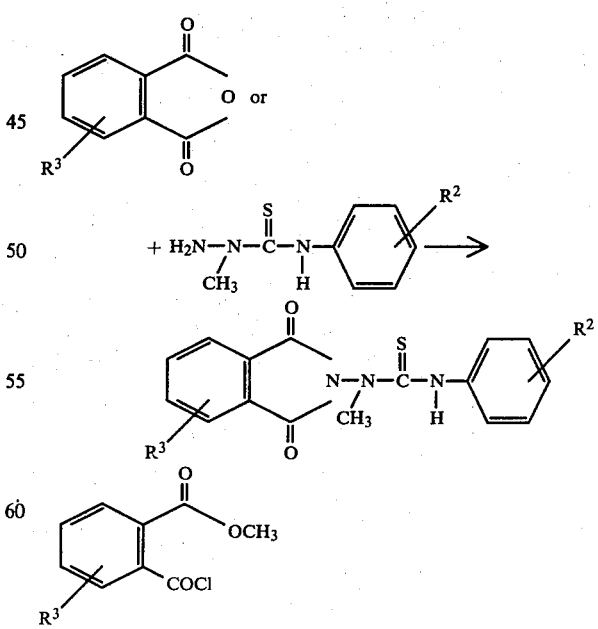

These methods are illustrated in the following specific procedures. The identity of the product was confirmed in each instance by means of infrared and nuclear magnetic resonance spectra. All melting points are as determined, uncorrected (Degrees C.).

N-METHYL-N-(PHENYLTHIOCARBAMOYL)-2-AMINO-1H-ISOINDOLE-1,3-(2H)DIONE (II)

To an ice-cold solution of 8.25 g (0.025 mole) of 2-(2-carboxybenzoyl)-1-methyl-N-phenylhydrazinethiocarboxamide in 225 ml of 1,2-dimethoxyethane at ~2° C., a solution of 5.5 g (0.027 mole) of N,N'-dicyclohexylcarbodiimide was added dropwise below 5° C. with stirring. The mixture was stirred in the ice bath and then left at room temperature overnight. The mixture was filtered to remove N,N'-dicyclohexylurea and the filtrate was evaporated below 40° C., under vacuum, to give a yellow amorphous solid which was stirred in 100 ml of dry ether and warmed gently. The ether solution was allowed to stand for a few hours and filtered to give 4.6 g (59%) of whitish yellow crystals, m.p. 142°–144°.

Recrystallization from ethyl acetate-hexane gave whitish crystals, m.p. 151°–153°.

Mass spectrum: M+311.

N-METHYL-N-(PHENYLTHIOCARBAMOYL)-2-AMINO-4-METHYL-1H-ISOINDOLE-1,3-(2H)DIONE

To a solution of 6.8 g (0.037 mole) of 1-methyl-N-phenylhydrazinethiocarboxamide and 3.0 g of pyridine in 100 ml dry dimethoxyethane, 2-carbomethoxy-6-methylbenzoyl chloride (8.0 g, 0.037 mole) was added and the resulting mixture was stirred at room temperature for 60 hours. The solvent was distilled and the residue was taken up in ethyl acetate, filtered and dried on anhydrous magnesium sulfate. Removal of the solvent gave 10 g (83%) of the desired product, m.p. 110°–115° (dec.).

2-AMINO-1H-ISOINDOLE-1,3-(2H)DIONE

To an ice-cold suspension of 14.7 g (0.1 mole) of phthalimide in 100 ml of 95% ethyl alcohol at 5° C., with stirring, 3.6 ml (0.11 mole) of 96.8% hydrazine was added dropwise. A slight exothermic reaction was observed and the mixture was allowed to stir at 5° C. for two hours. The mixture was diluted with 200 ml of ice water, stirred, filtered, washed with water and dried to give 12.2 g (75%) of white powder, m.p. 199°–202°.

Recrystallization from methanol-water gave white needles, m.p. 201°–203°.

N-(PHENYLTHIOCARBAMOYL)-2-AMINO-1H-ISOINDOLE-1,3-(2H)DIONE (IV)

To a suspension of 8.2 g (0.05 mole) of 2-amino-1H-isoindole-1,3-(2H)dione in 50 ml of dry 2-propanol, 6 ml (0.05 mole) of phenyl isothiocyanate was added. The mixture was stirred and refluxed for 3 hours, allowed to cool to room temperature and poured into 300 ml of 50% ethyl alcohol. After stirring for one hour, the solid which formed was filtered, washed with water and dried to give 12.1 g (81%) of the desired product as a white powder, m.p. 180°–181°. To make compounds in which Ar is benzoyl, benzoyl isothiocyanates may be employed in procedures of the type described above.

(EXAMPLE 1) PREPARATION OF 2-(1,2-DIMETHYL-3-PHENYLISOTHIOUREIDO)-1H-ISOINDOLE-1,3-(2H)-DIONE (III)

Method A

To a slurry of 3.3 g (0.01 M) of 2-(2-carboxybenzoyl)-1-methyl-N-phenylhydrazinethiocarboxamide and 4.1 g (0.03 m) of potassium carbonate in 100 ml of acetone, was added 4.3 g (0.03 m) of methyl iodide. After stirring at room temperature for 16 hrs, 500 ml of ice water was added and the pH adjusted to 3 with dil HCl. An oil separated which crystallized with continued stirring, was collected and washed with water to give 1.2 g (37% yield) of product, m.p. 88°–90°.

Method B

Six grams (0.019 m) of N-Methyl-N-(phenylthiocarbamoyl)-2-amino-1H-isoindole-1,3-2H-dione was dissolved in 2 ml of DMF and 5 ml of methyl iodide, then stirred at room temperature for 16 hours. To the solid mass was addd ethyl acetate and the crystals collected, washed with ethyl acetate and dried to give 7.3 g of hydroiodide salt, m.p. 145°–148° (dec).

The free base was obtained by suspending the salt in dil NH4OH and extracting with CHCl3 which was washed with water, sat. NaCl and dried over anhydrous Na2SO4. Removal of the CHCl3 at reduced pressure in a rotary evaporator gave a residual oil which was crystallized from ether-petroleum ether, wt. 4.6 g, m.p. 90°–91° (75%).

(EXAMPLE 2) PREPARATION OF 2-(2-METHYL-3-PHENYLISOTHIOUREIDO)-1H-isoindole-1,3-(2H)DIONE (V)

To 100 ml of dry acetone, 5.0 g (0.018 m) of N-(phenylthiocarbamoyl)-2-amino-1-H-isoindole-1,3-(2H)dione and 2.5 g (0.018 m) powdered anhydrous potassium carbonate was added. To this suspension 1.1 ml (0.018 m) of methyl iodide was added and the mixture was stirred overnight at room temperature. The mixture was poured into ~300 ml of water, stirred, filtered, washed with water and dried to give 4.4 g (78%) of a yellow powder, m.p. 161°–164°. Mass spectrum: M+311.

(EXAMPLE 3) PREPARATION OF 2-(1-ALLYL-2-METHYL-3-PHENYLISOTHIOUREIDO)-1-H-ISOINDOLE-1,3-(2H)DIONE

To 50 ml of dry acetone, 4.0 g (0.013 m) of the product of Example 2, 2.2 g (0.016 m) of powdered anhydrous potassium carbonate, and 1.4 ml (0.016 m) of allyl bromide was added in succession and the mixture stirred overnight at room temperature. The mixture was poured into 300 ml of ice water with stirring. The aqueous layer was decanted and the residue suspended in fresh ice cold water, stirred and filtered to give a yellow semisolid product. This was purified by stirring in hexane to give a yellow powder 1.8 g (39%), m.p. 78°–81°.

(EXAMPLE 4) PREPARATION OF 2-(1,2-DIALLYL-3-PHENYLISOTHIOUREIDO)-1-H-ISOINDOLE-1,3-(2H)DIONE

A mixture of 100 ml dry acetone, 5.0 g (0.018 m) N-(phenylthiocarbamoyl)-2-amino-1-H-isoindole-1,3-(2H)dione, 6.9 g (0.05 m) powdered anhydrous potassium carbonate, and 4.3 ml (0.05 m) allyl bromide was stirred overnight at room temperature and evaporated to dryness. The residue was suspended in 50 ml of cold water and the product was extracted with ether. The ether extract, on work-up, gave 4.7 g (69%) of thick yellow liquid.

USE OF THE GROWTH REGULATORS

The growth of plants may be regulated by applying the growth regulator compounds to the plants, either on seed, the soil or directly on the plants in an effective amount. If the objective is to combat unwanted vegetation, an amount sufficient to produce severe injury or abnormality of form of growth is usually sufficient. Sometimes the unwanted vegetation continues to live for a time but is stunted or distorted so that it cannot compete with crop plants and eventually succumbs to shading by the crop, or failure to obtain or to assimilate nutrients in the manner of a normal plant. An effect which is occasionally observed upon pre-emergent application is a loss of geotropic orientation upon germination of seed. In extreme cases roots may grow upward out of the soil, while leaves remain beneath the surface. Naturally the plants do not survive for long in this upside-down orientation. However, they can be transplanted and made to survive, which indicates that the growth regulant in one sense is not very phytotoxic. The survival rate of affected plants is much greater when the growth regulants are applied post-emergently, because the plants are already past the critical stages of emergence and growth of foliage and a root system. Retarded growth, with some abnormalities of form, accompanied by an increase in chlorophyl concentration in foliage is sometimes observed after post-emergent application. This combination of properties is particularly desirable for use on turf, to obtain a good color and reduce the frequency of cutting.

In highly active compounds, phytotoxic effects of pre-emergent and post-emergent application are often readily apparent. These effects may be demonstrated by means of the following illustrative procedures.

PRE-EMERGENT APPLICATION

Disposable paper trays about 2½ inches deep were filled with soil and sprayed with aqueous spray mixtures at a rate of 5 lb. of active chemical per acre of sprayed area, were seeded with 6 species of plant seeds and were then covered with about ¼ inch of soil. The spray mixtures were prepared by dissolving the proper amount of growth regulant compound in 15 ml of acetone, adding 4 ml of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 60 ml by addition of warm water. Twenty-one days after seeding and treatment the plantings were examined and plant injury was rated according to the following schedule.

DEGREE OF EFFECT

0 = no effect
1 = slight effect, plants recovered
2 = moderate effect, injury to 26 to 75 percent
3 = severe effect, injury to 76 to 99 percent of foliage
4 = maximum effect (all plants died).

POST-EMERGENT APPLICATION

Several species of plants were grown in potting soil in disposable styrofoam trays and tomatoes were grown in four-inch pots in the greenhouse. Aqueous spray formulations were prepared and the growing plants were sprayed at a spray volume of 60 gallons per acre and an application rate of 5 lb. per acre. Spray mixtures were prepared in the manner described above. For comparative purposes, plants were also sprayed at 60 gal./acre with a spray mixture containing no growth regulator. Plant injury was again rated according to the schedule disclosed above and observations of growth regulant effects in both pre- and post-emergent tests were observed and recorded as follows:

| Effect | Abbreviation in Tables |
|---|---|
| Formative effect on new growth | F |
| Epinasty | E |
| Growth reduction | G |
| Necrosis | N |
| Non-emergence | K |

In the table below there are tabulated various compounds which have been made according to the above illustrative procedures, as well as observations of pre- and post-emergent herbicidal and growth regulant effects. Some of the compounds were tested in the form of the hydrohalide salts, resulting from alkylation with alkyl halides. These compounds are identified under the column titled "salt type".

TABLE I

EFFECTS ON PLANT SPECIES
of Compounds of the formula

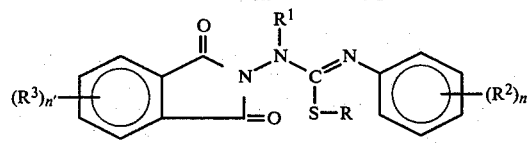

| Compound No. | R | R¹ | (R²)n | (R³)n' | Salt Type | M.P. °C. |
|---|---|---|---|---|---|---|
| 2878 | —CH₃ | —CH₃ | n = 0 | n' = 0 | | 88–90° |
| 2960 | allyl | —CH₃ | n = 0 | n' = 0 | | oil |
| 2961 | benzyl | —CH₃ | n = 0 | n' = 0 | | oil |
| 3062 | —CH₃ | —H | n = 0 | n' = 0 | | 161–4° |
| 3099 | —CH₃ | —CH₃ | 3-F | n' = 0 | | 62–5° |
| 3100 | —CH₂CH₃ | —CH₃ | n = 0 | n' = 0 | | 80–2° |
| 3101 | allyl | —CH₃ | 3-F | n' = 0 | | oil |
| 3102 | benzyl | —CH₃ | 3-F | n' = 0 | | oil |
| 3104 | —CH₃ | —CH₃ | 2,4-(CH₃)₂ | n' = 0 | | 107–9° |
| 3105 | n-propyl | —CH₃ | n = 0 | n' = 0 | | oil |
| 3110 | 4-Br—Benzyl | —CH₃ | n = 0 | n' = 0 | | oil |
| 3111 | —CH₂CO—C(CH₃)₃ | —CH₃ | n = 0 | n' = 0 | HBr | 135–8° |

TABLE I-continued

| | | | | | | |
|---|---|---|---|---|---|---|
| 3129 | —CH$_3$ | —CH$_3$ | 2,6-(CH$_3$)$_2$ | n' = 0 | | 137-40° |
| 3130 | —CH$_3$ | —CH$_3$ | 3,4-—CH=CH—CH=CH— | n' = 0 | | wax |
| 3134 | —CH$_3$ | —CH$_3$ | 2,4,5-(CH$_3$)$_3$ | n' = 0 | | oil |
| 3135 | —CH$_3$ | —CH$_3$ | 2,5-(CH$_3$)$_2$ | n' = 0 | | 122-4° |
| 3141 | —CH$_3$ | —CH$_3$ | n = 0 | n' = 0 | HI | 145-8° dec. |
| 3143 | Allyl | —CH$_3$ | n = 0 | n' = 0 | HBr | 117-8° |
| 3144 | benzyl | —CH$_3$ | n = 0 | n' = 0 | HBr | 147-8° |
| 3171 | —CH$_2$—CH$_2$— | | n = 0 | n' = 0 | | 75-80° |
| 3176 | —CH$_3$ | Allyl | n = 0 | n' = 0 | | 78-81° |
| 3191 | —CH$_3$ | —CH$_3$ | -2,3-(CH$_3$)$_2$ | n' = 0 | | 95-7° |
| 3192 | —CH$_3$ | —CH$_3$ | 4-phenoxy | n' = 0 | | 159-62° |
| 3193 | —CH$_3$ | —CH$_3$ | 4-n-butyl | n' = 0 | | oil |
| 3205 | —CH$_2$—C(=O)—O—Et | —CH$_3$ | n = 0 | n' = 0 | HBr | 166-8° |
| 3206 | " | —CH$_3$ | n = 0 | n' = 0 | | 67-70° |
| 3215 | —CH$_3$ | CH$_2$C≡CH | n = 0 | n' = 0 | | oil |
| 3216 | allyl | allyl | n = 0 | n' = 0 | | oil |
| 3218 | —CH$_3$ | —H | 4-CH$_3$ | n' = 0 | | 151-3° |
| 3219 | allyl | —H | 4-CH$_3$ | n' = 0 | | 128-30° |
| 3220 | —CH$_3$ | —CH$_3$ | 4-CH$_3$ | n' = 0 | | 111-114° |
| 3221 | —CH$_3$ | allyl | 4-CH$_3$ | n' = 0 | | oil |
| 3222 | allyl | —H | n = 0 | n' = 0 | | 60-61° |
| 3251 | 3,3-dimethyl allyl | —H | n = 0 | n' = 0 | | 115-7° |
| 3274 | —CH$_3$ | —CH$_2$—C(=O)—O—Et | n = 0 | n' = 0 | | oil |
| 3276 | —CH$_3$ | —H | -3-CH$_3$ | n' = 0 | | 158-9° |
| 3277 | —CH$_3$ | —CH$_3$ | -3-CH$_3$ | n' = 0 | | oil |
| 3278 | allyl | allyl | -3-CH$_3$ | n' = 0 | | oil |
| 3292 | —CH$_2$C≡CH | —CH$_3$ | -3-F | n' = 0 | HBr | 140-1° |
| 3293 | —CH$_2$C≡CH | —CH$_3$ | -3-F | n' = 0 | | 90-2° |
| 3294 | —CH$_3$ | —CH$_3$ | -3-Cl | n' = 0 | | oil |
| 3295 | —CH$_3$ | —CH$_3$ | -3,4-Cl$_2$ | n' = 0 | | 124-7° |
| 3296 | —CH$_3$ | —H | -3-Cl | n' = 0 | | 198-200° |
| 3297 | —CH$_3$ | —H | -3,4-Cl$_2$ | n' = 0 | | 182-3° |
| 3298 | —CH$_3$ | allyl | 3-Cl | n' = 0 | | 102-4° |

EFFECTS ON PLANT SPECIES
of Compounds of the formula

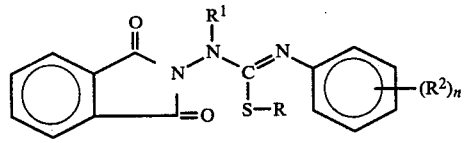

| Compound No. | R | R$^1$ | (R$^2$)n | Salt Type | M.P. °C. |
|---|---|---|---|---|---|
| 3283 | allyl | —CH$_3$ | 2,5-(CH$_3$)$_2$ | HBr | 129-130 |
| 3287 | allyl | —CH$_3$ | 2,5-(CH$_3$)$_2$ | | Syrup |
| 3409 | —CH$_2$COOC$_2$H$_5$ | " | 4-F | HBr | 169-171 |
| 3410 | —CH$_2$COOC$_2$H$_5$ | " | 4-F | | 83-85 |
| 3411 | —CH$_2$COOC$_2$H$_5$ | " | 3-F | HBr | 138-140 |
| 3497 | —C$_2$H$_5$ | —H | n = 0 | | 130-138 |
| 3500 | —C$_2$H$_5$ | allyl | n = 0 | | Syrup |
| 3627 | —CH$_3$ | —CH$_3$ | 3-CF$_3$ | | Oil |
| 3628 | —CH$_3$ | —CH$_3$ | 4-Cl | | 123-125 |
| 3629 | —CH$_2$CH$_2$CH$_2$— | | 4-Cl | | 100-130 |
| 3631 | benzyl | —H | 4-Cl | | 168-170 |
| 3632 | benzyl | —CH$_3$ | 4-Cl | | 113-115 |
| 3633 | benzyl | 2-propynyl | 4-Cl | | Oil |
| 3635 | benzyl | benzyl | 4-Cl | | 103-105 |
| 3637 | —CH$_3$ | acetyl | 3,4-Cl$_2$ | | 143-145 |

EFFECTS ON PLANT SPECIES
of Compounds of the formula

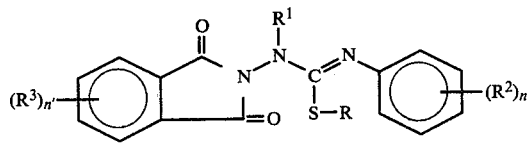

Compound

TABLE I-continued

| No. | R | R¹ | (R²)n | (R³)n' | Type | M.P. °C. |
|---|---|---|---|---|---|---|
| 3299 | —CH₃ | —CH₂C≡CH | 3-Cl | n' = 0 | | oil |
| 3300 | —CH₃ | —CH₂—C(=O)—O—Et | 3-Cl | n' = 0 | | oil |
| 3302 | —CH₃ | allyl | 3,4-Cl₂ | n' = 0 | | 90-2 |
| 3303 | —CH₃ | —CH₂C≡CH | 3,4-Cl₂ | n' = 0 | | oil |
| 3339 | —CH₃ | benzyl | 3,4-Cl₂ | n' = 0 | | oil |
| 3348 | —CH₂CH₂CH₂— | | n = 0 | n' = 0 | | 193-5 |
| 3340 | n-butyl | —H | -3,4-Cl₂ | n' = 0 | | 165-7 |
| 3342 | —CH₂—S—CH₃ | —H | -3-Cl | n' = 0 | | crude oil |
| 3344 | n-butyl | —CH₃ | 3,4-Cl₂ | n' = 0 | | 98-101 |
| 3346 | —CH₂—S—CH₃ | —CH₃ | 3-Cl | n' = 0 | | 77-80 |
| 3328 | —CH₃ | —H | n = 0 | -3-CH₃ | | 180-4 |
| 3329 | —CH₃ | —CH₃ | n = 0 | -3-CH₃ | | oil |
| 3331 | —CH₃ | —CH₃ | n = 0 | -3-CH₃ | | 135-136 |
| 3332 | —CH₃ | —H | n = 0 | 4,5,6,7-tetrachloro | | 265-70 |

EFFECTS ON PLANT SPECIES
of Compounds of the formula

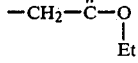

| Compound No. | R | R¹ | (R²)ₙ | Salt Type | M.P. °C. |
|---|---|---|---|---|---|
| 3700 | —CH₃ | —CH₃ | 4-NO₂ | | 152-155 |
| 3701 | benzyl | —H | 4-NO₂ | | 182-184 |
| 3702 | —CH₂COC₆H₅ | " | —H | | 149-152 |
| 3703 | 4-pentenyl | " | —H | | 79-81 |
| 3704 | 2,6-dichloro-benzyl | —H | —H | | 176-178 |
| 3705 | 4-methyl-benzyl | —H | —H | | 163-165 |
| 3706 | 3-phenoxy-propyl | —H | —H | | 100-103 |
| 3707 | benzyl | —CH₃ | 4-NO₂ | | 122-125 |
| 3708 | benzyl | 2-propynyl | 4-NO₂ | | 94-97 |
| 3709 | 2,6-dichloro-benzyl | —CH₃ | —H | | 165-167 |
| 3710 | 4-methyl-benzyl | —CH₃ | —H | | Oil |
| 3731 | —CH₃ | —H | 4-OCH₃ | | 197-199 |
| 3732 | —C₂H₅ | —H | 4-OCH₃ | | 195-197 |
| 3733 | —CH₃ | —CH₃ | 3-Cl₁ 4-CH₃ | | 126-129 |
| 3734 | —C₂H₅ | —H | 3-Cl₁ 4-CH₃ | | 166-168 |
| 3749 | propyl | —H | —H | | 104-106 |
| 3750 | propyl | allyl | —H | | 80-82 |
| 3751 | isopropyl | —H | —H | | 132-134 |
| 3752 | isopropyl | —CH₃ | —H | | dec. 85 |
| 3780 | —CH₃ | —CH₃ | 4-OCH₃ | | 105-108 |
| 3781 | —C₂H₅ | —CH₃ | 4-OCH₃ | | 85-88 |
| 3782 | —C₂H₅ | —CH₃ | 3Cl— 4-CH₃ | | 104-106 |
| 3783 | —CH₃ | —CH₃ | 2-CH₃ | | Oil |
| 3784 | —C₂H₅ | —H | 2-CH₃ | | 135-137 |
| 3785 | —C₂H₅ | —CH₃ | 2-CH₃ | | Oil |
| 3786 | —CH₃ | —CH₃ | 2-Cl | | Oil |
| 3787 | —C₂H₅ | —H | 2-Cl | | 116-118 |
| 3788 | —CH₃ | —CH₃ | 4-F | | 82-85 |
| 3789 | —C₂H₅ | —H | 4-F | | 183-185 |
| 3790 | —CH₃ | —H | 3-F | | 204-206 |
| 3791 | —C₂H₅ | —CH₃ | 2-Cl | | Oil |
| 3792 | —C₂H₅ | —CH₃ | 4-F | | Oil |
| 3793 | —CH₃ | —H | 2-CH₃ 3-Cl | | 165-168 |
| 3794 | —CH₃ | —H | 4-butyl | | 127-130 |
| 3795 | —C₂H₅ | —H | 4-butyl | | 107-109 |
| 3796 | —CH₃ | —CH₃ | 4-isopropyl | | 111-114 |
| 3797 | —C₂H₅ | —H | 4-C₃H₇ | | 142-144 |
| 3798 | —CH₃ | —CH₃ | 2-Cl₁ 6-CH₃ | | 106-108 |

TABLE I-continued

| | | | | |
|---|---|---|---|---|
| 3799 | —$C_2H_5$ | —H | 2-$Cl_1$ 6-$CH_3$ | 172–174 |
| 3800 | benzyl | —H | —H | 115–116 |
| 3812 | ispropyl | allyl | —H | 87–90 |
| 3813 | butyl | —H | —H | 119–121 |
| 3814 | butyl | —$CH_3$ | —H | dec.65 |
| 3815 | butyl | allyl | —H | Syrup |
| 3816 | isobutyl | —H | —H | 137–139 |
| 3849 | isobutyl | —$CH_3$ | —H | dec.65 |
| 3850 | isobutyl | allyl | —H | 62–65 |
| 3851 | —$CH_2COC_2H_5$ (O) | —H | —H | semi-solid |
| 3977 | —CN | —$CH_3$ | n = 0 | dec.145 |
| 4017 | —$CH_3$ | —H | 3-benzyloxy | 106–108 |
| 4019 | —$CH_3$ | —H | 3-$NO_2$ | 191–193 |
| 4020 | —$C_2H_5$ | —H | 3-$NO_2$ | 192–195 |
| 4021 | —$CH_3$ | —H | 4-benzyloxy | 130–133 |
| 4023 | —$CH_3$ | —$CH_3$ | 3-$CF_3$—4-Cl | 95–97 |
| 4025 | —$CH_3$ | —H | 2-$CF_3$ | 156–159 |
| 4026 | —$CH_3$ | —$CH_3$ | 3-benzyloxy | 83–85 |
| 4027 | —$CH_3$ | —$CH_3$ | 3-$NO_2$ | |
| 4028 | —$CH_3$ | —$CH_3$ | 4-benzyloxy | 87–90 |
| 4029 | —$CH_3$ | —$CH_3$ | 2,6-$Cl_2$ | Oil |
| 4030 | —$CH_3$ | —$CH_3$ | 2-$CF_3$ | Oil |
| 4033 | —$CH_3$ | —H | 3-$OCH_3$ | 158–160 |
| 4034 | —$C_2H_5$ | —H | 3-$OCH_3$ | 103–105 |
| 4035 | —$CH_3$ | —H | 3,5-$(CH_3)_2$ | 200–202 |
| 4036 | —$C_2H_5$ | —H | 3,5-$(CH_3)_2$ | 129–131 |
| 4062 | 2-(2,4-dichlorophenoxy)ethyl | —$CH_3$ | n = 0 | 108–110 |
| 4063 | —$CH_3$ | —$CH_3$ | 3-$OCH_3$ | 85–88 |
| 4064 | —$CH_3$ | —$CH_3$ | 3-$SCH_3$ | 91–94 |
| 4065 | —$C_2H_5$ | —H | 3-$SCH_3$ | 127–129 |
| 4066 | —$CH_3$ | —$CH_3$ | 2-$Cl_1$ 4-$CH_3$ | 90–92 |
| 4068 | —$CH_3$ | —$CH_3$ | 3-$CCH_3$ (‖ O) | 109–111 |
| 4070 | —$CH_3$ | —$CH_3$ | 4-$COCH_3$ | 144–145 |
| 4115 | —$CH_3$ | —$CH_3$ | 4-CN | 175–178 |
| 4116 | —$CH_3$ | —H | 4-$N(C_2H_5)_2$ | 187–188 |
| 4117 | —$CH_3$ | —$CH_3$ | 4-$CF_3$ | 131–133 |
| 4118 | —$CH_3$ | —$CH_3$ | 2-$CH_3$—4-Cl | 86–88 |
| 4119 | —$CH_3$ | —$CH_3$ | 3,4-$OCH_2O$— | 114–117 |
| 4120 | —$CH_3$ | —$CH_3$ | 2,4-$Cl_2$ | 84–86 |
| 4121 | —$C_2H_5$ | —H | 2,4-$Cl_2$ | 128–130 |
| 4122 | —$CH_3$ | —H | 4-OEt | 162–165 |
| 4123 | —$C_2H_5$ | —H | 4-OEt | 142–144 |
| 4124 | —$CH_3$ | —H | -2-F | 139–141 |
| 4125 | —$C_2H_5$ | —H | 2-F | 110–112 |
| 4126 | —$CH_3$ | —$CH_3$ | 4-OEt | 114–116 |
| 4127 | —$CH_3$ | —$CH_3$ | 2-F | 87–89 |
| 4128 | —$C_2H_5$ | —$CH_3$ | 2,4-$Cl_2$ | 86–88 |
| 4129 | —$C_2H_5$ | —$CH_3$ | 4-OEt | 102–106 |
| 4130 | —$C_2H_5$ | —$CH_3$ | 2-F | 79–81 |
| 4259 | —$CH_3$ | —$CH_3$ | 3,4-$CH_2CH_2CH_2$— | Semi-solid |
| 4261 | —$CH_3$ | —$CH_3$ | 3-COOEt | 143–146 |
| 4262 | —$C_2H_5$ | —$CH_3$ | 3,4-$CH_2CH_2CH_2$— | Oil |
| 4263 | —$C_2H_5$ | —$CH_3$ | 3-COOEt | 98–101 |
| 4264 | propyl | —$CH_3$ | 2,4-$Cl_2$ | 85–87 |
| 4290 | —$CH_2CH=CH_2$ | —$CH_3$ | 4-$CF_3$ | Oil |
| 4291 | 2-(2,4-dichlorophenoxy)ethyl | —$CH_3$ | 2-F | Oil |
| 4292 | —$CH_2CH=CH_2$ | —$CH_3$ | 3,4-$OCH_2O$— | Oil |
| 4293 | 4-fluorobenzoylmethyl | —H | 4-F | 98–101 |
| 4329 | 1-benzoylethyl | —$CH_3$ | 4-$OCH_3$ | 80–83 |
| 4330 | 4-fluorobenzoylmethyl | —$CH_3$ | 2-$CH_3$ | 78–81 |
| 4331 | 4-fluorobenzoylmethyl | —$CH_3$ | 2-Cl | 75–78 |

TABLE I-continued

| | | | | | |
|---|---|---|---|---|---|
| 4332 | 4-fluoro-benzoylmethyl | —CH₃ | 2-F | | 60–63 |
| 4333 | 2-(N-ethyl-N-phenyl-carbamyl)ethyl | —H | n = 0 | | 184–186 |
| 4355 | —CH₂COOH | —CH₃ | n = 0 | HBr | 115–120 |
| 4373 | —CH₃ | 2-phenoxyethyl | n = 0 | | Glass |
| 4374 | —CH₃ | —CH₂CH₂OCH=CH₂ | n = 0 | | 147–149 dec. |
| 4375 | —CH₃ | 3-chlorobenzyl | n = 0 | | Glass |
| 4429 | —CH₃ | isopropyl | n = 0 | | 116–118 |
| 4230 | —C₂H₅ | isopropyl | n = 0 | | 170–172 |
| 4496 | 4-pyridylmethyl | H | n = 0 | | 183–185 |
| 4497 | 2-pyridylmethyl | H | n = 0 | | 168–171 |
| 4498 | 3-pyridylmethyl | H | n = 0 | | 202–205 |
| 4499 | 4-pyridylmethyl | H | 3-F | | 75–80 |
| 4500 | 2-pyridylmethyl | H | 3-F | | 195–197 |
| 4501 | 3-pyridylmethyl | H | 3-F | | 183–186 |
| 4502 | 4-pyridylmethyl | —CH₃ | n = 0 | | 110–115 |
| 4503 | 3-pyridylmethyl | —CH₃ | n = 0 | | 79–81 |
| 4504 | 2-pyridylmethyl | —CH₃ | 3-F | | 109–112 |
| 4505 | 3-pyridylmethyl | —CH₃ | 3-F | | 170–175 |
| 4455 | —CH₂CNH—[triazole]—CF₃ (with C=O) | —H | n = 0 | | 213–215 |
| 4456 | —C(CH₃)₂—benzoyl | —H | n = 0 | | 193–196 |
| 4457 | 3-phenylallyl | —CH₃ | n = 0 | | Oil |
| 4458 | 3-phenylallyl | —H | 3F | | Oil |
| 4459 | —C(CH₃)₂—benzoyl | —H | 3F | | 150–153 |
| 4460 | —CH₂CH₂CF=CF₂ | —H | n = 0 | | 110–112 |
| 4461 | 2-(N-ethyl-N-phenyl-carbamyl)ethyl | —CH₃ | 3-F | | Oil |
| 4462 | —CH₂CH₂CF=CF₂ | —CH₃ | 3-F | | 60–62 |
| 4463 | —CH₂CH₂CF=CF₂ | —CH₃ | n = 0 | | Oil |
| 4313 | —CH₃ | —CH₃ | n = 0 | | 134–138 |
| 4359 | —CH₃ | —C₂H₅ | n = 0 | | 114–116 |
| 4360 | —C₂H₅ | —C₂H₅ | n = 0 | | 107–108 |

EFFECTS ON PLANTS SPECIES
of Compounds of the formula

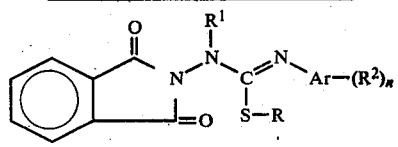

| Compound No. | R | R¹ | Ar (R²)ₙ | M.P. °C. |
|---|---|---|---|---|
| 4258 | —CH₃ | —CH₃ | 3-methylbenzoyl | 169–172 |

EFFECTS ON PLANT SPECIES
of Compounds of the formula

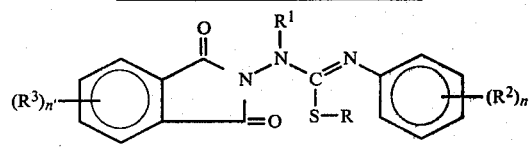

TABLE I-continued

| Compound No. | Preemergent Effects | | | | | | Postemergent Effects | | | | | | Comments on Utility |
|---|---|---|---|---|---|---|---|---|---|---|---|---|---|
| | Crab-grass | Cox-comb | Brome | Millet | Radish | Sugar Beet | Millet | Al-falfa | Oat | Radish | Sugar Beet | Toma-to | |
| 2878 | K4 | F3G3 | F3G3 | F3G3 | F3G2 | K4 | N2G3 F1 | F3G2 | 0 F1 | N2G1 F2 | F2G2 | F3 | Increases chlorophyl in foliage. |
| 2960 | F3G3 | F3G3 | F3G3 | F3G3 | F3G2 | K4 | N2G2 | F2G2 | N1G1 | N1G2 | F1G2 | F2 | Increases chlorophyl in foliage. Epinesty on alfalfa. |
| 2961 | K4 | F3G3 | F3G3 | F3G3 | F2G2 | K4 | N2G2 | F2G2 | F2G2 | F2G3 | F1G2 | F3G2 | Increases pod set of soybeans. |
| 3062 | 0 | 0 | 0 | 0 | 0 | 0 | 0 | 0 | 0 | 0 | F2G2 | 0 | |
| 3099 | F3G3 | F2G2 | F3G3 | F3G3 | F3G2 | K4 | F1G2 F2 | F3G2 | F1G1 | F3G2 F2 | F1G3 | N1F2 | Defoliates cotton. Kills pigweed. |
| 3100 | K4 | F2G2 | F3G3 | F3G3 | F2G2 | K4 | N1G1 F2 | F3G2 F2 | N1 | N1G2 F1 | F2G2 | F3 | Defoliates cotton. Kills pigweed. |
| 3101 | F3G2 | F2G1 | F3G3 | F2G3 | F2G1 | F2G2 | N1G1 F1 | N2G2 | N1F2 | N1G2 | F2G2 | F2G1 | Defoliates cotton. Kills pigweed. |
| 3102 | F2G1 | F1G1 | F2 | F3G2 | F1G1 | F1 | N1G1 | F2G1 | N1F1 | F2G2 | F2G2 | F3G1 | |
| 3104 | F1G1 | 0 | F2 | F2 | F1 | F1 | N1 F3 | F1 | N1G1 | F1 | F2G1 | F2 | |
| 3105 | F3G3 | F2G1 | F3G3 | F3G3 | F3G2 | K4 | N1G3 F1 | F3G2 | N1F1 | F1G2 | F2G2 | F2 | Defoliates cotton. Kills pigweed. |
| 3110 | K4 | F2G1 | F3G2 | F3G3 | F2G2 | K4 | N1G2 F2 | F2G2 | N1G1 | F1G1 | F2G2 | F2 | Controls pigweed. |
| 3111 | F3G3 | F2G1 | F3G3 | F3G3 | F2G1 | K4 | N1G2 | F3G2 | F2 | F2G2 | F2G2 | F3G2 | Promotes tillering of oats. |
| 3129 | 0 | 0 | 0 | 0 | 0 | 0 | 0 | 0 | 0 | 0 | N1F1 | 0 | |
| 3130 | | | | | | | | F2 | 0 | | F2 | F3 | Kills lambsquarter (post-emerg.) |
| 3134 | 0 | 0 | 0 | 0 | 0 | 0 | 0 | F1 | N1 | 0 | F2G1 | F2 | |
| 3135 | F1G1 | 0 | F1 | F2G2 | G2 | 0 | F2G1 F2 | F2 F3 | F1 | F1 F2 | F2G2 | F3 | Defoliates cotton. Kills pigweed. |
| 3141 | K4 | F3G3 | K4 | K4 | F3G3 | K4 | N3G3 F2 | N2G3 | F1G2 | N2G3 | N2G3 | F3 | |
| 3143 | F3G3 | F2G2 | F3G3 | F3G3 | F2G2 | K4 | N2G3 F1 | F3G2 | F1 | F2G2 F2 | F2G1 | F3G1 | Controls pigweed. Defoliates cotton. |
| 3144 | K4 | N4 | F3G3 | F3G3 | F2G2 | F2G1 | N2G1 | F3G2 | N1F1 | N1G2 F1 | F2G2 | F3 | Kills pigweed. |
| 3171 | 0 | 0 | 0 | 0 | 0 | 0 | 0 | F1 | N1 | N1G1 | F1 | F2 | |
| 3176 | F3G3 | F3G3 | F3G3 | F3G3 | F2G2 | F3G3 | F2 | F3G2 | N1F2 | F1 | F2G3 | F3 | Promotes tillering of oats |
| 3191 | F1G1 | F1 | F3G1 | F3G3 | F3G2 | F3G2 | N1F1 | F2 | F1 | F2 | F2G2 | F2 | |
| 3192 | 0 | 0 | 0 | 0 | 0 | 0 | 0 | 0 | 0 | 0 | F1 | 0 | |
| 3193 | 0 | 0 | F2 | 0 | 0 | 0 | 0 F3 | F1 F3 | F1 | F1 | F1G3 | 0 | |
| 3205 | K4 | K4 | F3G3 | F3G3 | F3G2 | F3G3 | N3G3 F2 | G3 | F1G2 | F2G2 | F2G3 | F3 | |
| 3206 | F3G3 | F3G3 | F3G3 | F3G3 | F3G2 | K4 | N1G2 | F2G3 | 0 | F2G2 | F2G3 | F3 | |
| 3215 | F3G2 | F2G1 | F3G3 | F3G2 | F2G2 | F3G3 | 0 | G2F3 | F1 | F2 | F2G2 | F3G1 | |
| 3216 | F3G3 | F3G3 | K4 | F3G3 | F3G2 | F3G3 | F1 | F3 F2 | F2 | F2 | F2G3 | F2 | Increases tomato fruit set.(Heart shaped fruit) |
| 3218 | 0 | 0 | F1 | 0 | 0 | 0 | 0 | N1G2 | 0 | N1 | F3G2 | 0 | |
| 3219 | F1G1 | 0 | F2 | 0 | 0 | 0 | N1 F3 | F3G2 | F1 | F1 | F2G2 | F1 | |
| 3220 | F3G3 | F2G2 | K4 | F3G3 | F3G3 | F2G2 | N1G2 | F3G2 | F1 | F1G1 | F3G3 | F3G1 | |
| 3221 | F3G3 | F3G3 | F3G2 | F3G3 | F3G2 | F2G2 | F1 | F1G1 | F1 | F2 | F2G2 | F1G1 | |
| 3222 | F1 | 0 | F1 | 0 | 0 | 0 | 0 | F2G1 | 0 | 0 | F1G2 | 0 | Increases tomato fruit set. |
| 3251 | 0 | 0 | 0 | 0 | 0 | 0 | 0 | F1 | 0 | 0 | 0 | 0 | |
| 3274 | F1 | 0 | F2 | F2 | F1 | 0 | N1 | N1F1 | 0 | N1G1 | F2G3 | N1F1 | |
| 3276 | 0 | 0 | F2 | F2 | 0 | 0 | 0 | F2 | 0 | F1 | F2G2 F2 | 0 | |
| 3277 | F3G3 | F2G2 | F3G3 | F3G3 | F3G2 | F3G2 | F1G1 | F3G3 | F1G1 | F2G1 | N2G3 | F2 | Increases tomato fruit set, tillering of oats. |
| 3278 | F2G1 | F2 | F2 | F2G1 | F1G1 | F1G1 | 0 | F2G1 | F1 | 0 | F3G2 | 0 | |
| 3292 | F3G3 | F3G2 | F3G3 | F3G3 | F3G3 | F3G3 | N1G2 | F3G2 | F2 | F3G2 | F2G3 | F2 | Increases fruit set on tomatoes, tillering of oats, controls crabgrass. |
| 3293 | | | | | | | | | | | | | |
| 3294 | F2G2 | F2G2 | F3G3 | F3G2 | F2G2 | K4 | F1G1 | F3G2 | F2 | F3G2 | F3G2 | F1 | Increases tomato fruit set, tillering of oats, controls crabgrass. |
| 3295 | F2 | F1 | F2 | F1 | F1 | F1 | 0 | F3G2 | F1 | F2G2 | F3G3 | F2 | Increases tillering of oats. |
| 3296 | 0 | 0 | F1 | F1 | 0 | 0 | 0 | F1 | 0 | 0 | F2G2 | 0 | |
| 3297 | 0 | 0 | 0 | 0 | 0 | 0 | 0 | F1 | 0 | 0 | F1G1 | F1 | |
| 3298 | | | | | | | | | | | | | |

EFFECTS ON PLANT SPECIES
of Compounds of the formula

TABLE I-continued

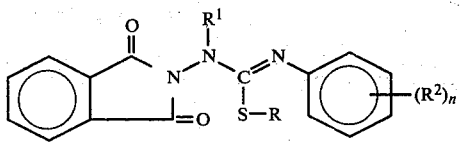

| Compound No. | Preemergent Effects | | | | | | Postemergent Effects | | | | | | Comments on Utility |
|---|---|---|---|---|---|---|---|---|---|---|---|---|---|
| | Crab-grass | Cox-comb | Brome | Millet | Radish | Sugar Beet | Millet | Al-falfa | Oat | Radish | Sugar Beet | Toma-to | |
| 3283 | F1 | F1 | F2 | F2G2 | F1 | F1 | 0 | 0 | 0 | F1G1 | F2G3 | N1 | |
| 3287 | 0 | F1 | F1 | F2G1 | F1G1 | F1G1 | 0 F2 | 0 | F1 F1 | 0 | F1G2 | N1 | |
| 3409 | F3G3 | K4 | K4 | F3G3 | F3G3 | K4 | N1G2 F2 | F3G3 | N1G1 | F3G3 | F3G2 | F3 | |
| 3410 | F3G3 | K4 | K4 | F3G3 | F3G3 | K4 | N1G2 | F3G3 | G2 | F2G2 F1 | F3G3 | F3 | |
| 3411 | F3G3 | K4 | K4 | F3G3 | K4 | K4 | N2G3 | F3G2 | G2F1 | N2G3 | F2G3 | F2G3 | |
| 3497 | F2G2 | F1 | F3G1 | F3G1 | F1G1 | F2G1 | 0 | F2G1 | 0 | N1 | F3G1 | F3 | |
| 3500 | F1G1 | F2G1 | F3G2 | F2G2 | F2G2 | F2G2 | F1G1 | F2G1 | F1G1 | F1 | F3G1 | F2 | |
| 3672 | F1G1 | K4 | F3G3 | F1G1 | F2G2 | F3G2 | 0 | F2G1 | F1G1 | F2G1 | F3G2 | F2 | Increases fruit set |
| 3628 | F3G3 | F3G3 | K4 | F3G3 | F3G2 | F3G3 | G2F1 | F3G3 | G2F1 | F2G1 | F3G2 | F3 | Increases fruit set |
| 3629 | 0 | 0 | F2 | 0 | 0 | 0 | 0 | F1 | 0 | F1 | F2 | F1 | |
| 3631 | 0 | 0 | F2 | 0 | 0 | 0 | 0 | F1 | 0 | 0 | F2 | 0 | |
| 3632 | F3G3 | F2G2 | K4 | F3G2 | F3G2 | F3G2 | G1 | F3 | G1 | F1G1 | F3G1 | F3G2 | Increases fruit set |
| 3633 | F3G2 | F2G1 | F3G3 | F2G1 | F3G2 | F2G1 | 0 | F2 | 0 | F1 | F3G1 | F3G1 | Increases fruit set |
| 3635 | 0 | F1 | F2 | 0 | F1 | F1 | 0 | F2 | 0 | F1 | F2G2 | F2 | Increases fruit set |
| 3637 | 0 | 0 | 0 | 0 | 0 | 0 | 0 | F2 | 0 | F1 | F2 | 0 | |

EFFECTS ON PLANT SPECIES
of Compounds of the formula

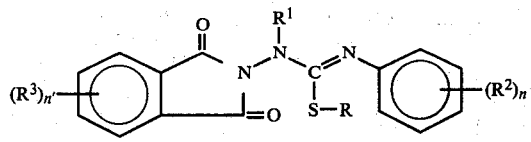

| Compound No. | Preemergent Effects | | | | | | Postemergent Effects | | | | | | Comments on Utility |
|---|---|---|---|---|---|---|---|---|---|---|---|---|---|
| | Crab-grass | Cox-comb | Brome | Millet | Radish | Sugar Beet | Millet | Al-falfa | Oat | Radish | Sugar Beet | Toma-to | |
| 3299 | F1 | F1 | F2 | F1 | F1 | F1 | 0 | F2G1 | 0 | F1 | F2G3 | 0 | |
| 3300 | 0 | 0 | 0 | 0 | 0 | 0 | N1 | F1 | 0 | 0 | F2G3 | 0 | |
| 3302 | 0 | 0 | 0 | 0 | 0 | 0 | 0 | F2 | 0 | 0 | F1G1 | 0 | |
| 3303 | 0 | 0 | 0 | 0 | 0 | 0 | 0 | F2 | 0 | 0 | F1G1 | 0 | |
| 3339 | 0 | 0 | 0 | 0 | 0 | 0 | 0 | 0 | 0 | 0 | F1 | F1 | |
| 3348 | 0 | 0 | 0 | 0 | 0 | 0 | 0 | 0 | 0 | 0 | F1 | F1 | |
| 3340 | 0 | 0 | 0 | 0 | 0 | 0 | 0 | 0 | 0 | 0 | F1 | F1 | |
| 3342 | 0 | F1 | F2 | 0 | F1 | F1G1 | 0 | F2G1 | 0 | F1 | F3G3 | 0 | |
| 3344 | F1G1 | F2G1 | F3G3 | F1 | F1G1 | F3G3 | 0 | F2 | 0 | F2 | F3G3 | F1 | Increased fruit set |
| 3346 | F3G3 | K4 | F3G3 | F3G2 | F2G2 | K4 | F2 | F3G2 | F2G1 | F2G1 | F2G3 | F2 | Increased fruit set |
| 3328 | 0 | 0 | 0 | 0 | N1 | 0 | 0 | 0 | 0 | 0 | F1 | 0 | |
| 3329 | F2G2 | F3G3 | F3G3 | F3G3 | F3G2 | F2G2 | F1G2 | F3G2 | F1 | N1F2 | F3G2 | N1F1 | |
| 3331 | K4 | F3G3 | F3G3 | K4 | F3G3 | F3G3 | N2G3 | F3G3 | F1 | F2G2 | F3G2 | F1 | |
| 3332 | 0 | 0 | 0 | 0 | 0 | 0 | 0 | 0 | 0 | 0 | F1 | 0 | |

EFFECTS ON PLANT SPECIES
of Compounds of the formula

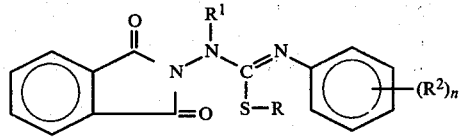

| Compound No. | Preemergent Effects | | | | | | Postemergent Effects | | | | | | Comments on Utility |
|---|---|---|---|---|---|---|---|---|---|---|---|---|---|
| | Crab-grass | Cox-comb | Brome | Millet | Radish | Sugar Beet | Millet | Al-falfa | Oat | Radish | Sugar Beet | Toma-to | |
| 3700 | 0 | 0 | F1 | 0 | 0 | 0 | 0 | F1 | F2 | F2G2 | F3G2 | F2 | Oat tillered increased fruit set |
| 3701 | 0 | 0 | 0 | 0 | 0 | 0 | 0 | G2F1 | 0 | F1 | F2 | N1 | |
| 3702 | 0 | 0 | F1 | 0 | 0 | 0 | 0 | F1 | F1 | F1 | F3 | N1 | |
| 3703 | 0 | 0 | 0 | 0 | 0 | 0 | 0 | F2G2 | F1 | 0 | F3 F2 | 0 | |
| 3704 | 0 | 0 | 0 | 0 | 0 | 0 | 0 | 0 | — | 0 | 0 | N1G1 | All plants taller except tomato |

TABLE I-continued

| | | | | | | | | | | | | |
|---|---|---|---|---|---|---|---|---|---|---|---|---|
| 3705 | 0 | 0 | 0 | 0 | 0 | 0 | N1 | F2 | 0 | F1 | N1F1 | F1 | |
| 3706 | 0 | 0 | 0 | 0 | 0 | 0 | 0 | F2 | 0 | F1 | F3G1 | F1 | Alfalfa very tall |
| 3707 | 0 | 0 | 0 | 0 | 0 | 0 | 0 | F1 | 0 | F1 | F2G2 | F2 | Increased fruit set |
| 3708 | 0 | 0 | 0 | 0 | 0 | 0 | 0 | 0 | 0 | F1 | F2 | 0 | |
| 3709 | F2G1 | F2G1 | F2 | F1G1 | F3G3 | F2G1 | 0 | F2G1 | 0 | F1 | F3G2 | F2 | Increased fruit set |
| 3710 | F3G3 | F3G2 | F3G3 | F3G2 | F3G3 | F3G3 | F2G1 | F3G1 | F2 | F2G2 | F3G2 | F2G1 | Increased fruit set and oat tillers |
| 3731 | 0 | F1 | F2 | 0 | G1 | F2 | 0 | F2 | F1 | F1 | F3 | N1F2 | Increased fruit set |
| 3732 | 0 | 0 | 0 | 0 | 0 | 0 | 0 | 0 | 0 | 0 | F2 | 0 | |
| 3733 | 0 | 0 | 0 | 0 | 0 | 0 | 0 | F1 | 0 | F2 | F3G1 | F2 | Increases fruit set |
| 3734 | 0 | 0 | 0 | 0 | 0 | 0 | 0 | 0 | 0 | 0 | F1 | 0 | |
| 3749 | 0 | 0 | 0 | 0 | 0 | 0 | 0 | 0 | 0 | 0 | F3G1 | 0 | |
| 3750 | F1 | F1 | F3G3 | F2G2 | F1 | F1 | 0 | F2G2 | F1N1 | F2G1 | F3G1 | F2G2 | Increased oat tillered fruit set |
| 3751 | 0 | 0 | 0 | 0 | 0 | 0 | 0 | F1 | 0 | 0 | F1 | N1 | |
| 3752 | K4 | F1G1 | K4 | F2G2 | F2G2 | K4 | F1G3 | F2G3 | G1 | F2 F2 | F2G1 | F3 | Increased fruit set |
| 3780 | F1 | F2G1 | F3G3 | F2G1 | F2G2 | F2G1 | N1 | F2G2 | N1 | N1G2 F2 | F3G1 | F1 | |
| 3781 | F2G1 | — | K4 | F2G2 | F3G2 | F2G2 | 0 | F3G2 | F2 | N2G2 | F3 | N1F2 | |
| 3782 | 0 | F1 | F2 | 0 | 0 | F1 | 0 | F2 | 0 | F2 | F3 | N1F1 | Increased fruit set |
| 3783 | F1 | F1 | F3G2 | F2G2 | F2G1 | F2 | N1G1 | N1 | G1 | F1G1 | F2G2 | F2 | Increased fruit set |
| 3784 | 0 | 0 | F1 | 0 | 0 | 0 | 0 | 0 | 0 | 0 | F2G1 | F1 | |
| 3785 | F2G1 | F2G2 | F3G3 | F3G2 | F3G3 | F3G2 | N1G2 | F2G2 | G1 | F2G2 | F3G2 | F2G1 | Increases fruit set |
| 3786 | F1G1 | F3G3 | F3G3 | F2G2 | F3G3 | F3G2 | F1G1 | F1 | — | F2 | F3G1 | F2 | Increases fruit set |
| 3787 | 0 | 0 | F1 | 0 | 0 | 0 | N1 | 0 | 0 | F1 F2 | F2G1 F1 | N1 | |
| 3788 | F3G3 | K4 | K4 | F3G2 | K4 | K4 | F3G2 | F2G3 | N1G2 | N1G3 | N1G2 | F2 | Increases fruit set |
| 3789 | 0 | F1 | F1 | 0 | 0 | 0 | 0 | F1 | 0 | 0 | F2G1 | 0 | |
| 3790 | 0 | 0 | F2 | 0 | 0 | 0 | 0 | F3 | 0 | 0 | F1G2 | N1F1 | Increases fruit set |
| 3791 | F2G1 | F2G2 | F3G2 | F2G2 | F3G2 | 0 | F1 | G1 | N1G1 | F2G2 | F2G1 | Increases fruit set |
| 3792 | F1G1 | F2G1 | F3G3 | F3G3 | F3G3 | K4 | F2G2 | F2G3 | G1F1 | F3G3 | F2G3 | F2G2 | Increases fruit set |
| 3793 | 0 | 0 | F1 | 0 | 0 | F1 | 0 | 0 | 0 | F1G1 | F2G1 | 0 | |
| 3794 | 0 | 0 | F2 | 0 | 0 | F1 | 0 | F1 | 0 | F1 | F1G1 | 0 | |
| 3795 | 0 | 0 | 0 | 0 | 0 | 0 | 0 | 0 | 0 | 0 | F1 | F1 | |
| 3796 | 0 | 0 | K3G3 | 0 | 0 | F1 | 0 | 0 | 0 | F2 | F2G2 | F2 | Increases fruit set |
| 3797 | 0 | 0 | F1 | 0 | 0 | K3G3 | 0 | 0 | 0 | 0 | F1 | 0 | |
| 3798 | 0 | 0 | 0 | 0 | 0 | 0 | 0 | 0 | 0 | 0 | F1 | 0 | |
| 3799 | G1 | 0 | N3G1 | 0 | 0 | 0 | 0 | 0 | 0 | F1 | F1 | 0 | |
| 3800 | 0 | 0 | F2 | 0 | 0 | F1 | 0 | 0 | 0 | 0 | — | N1 | |
| 3812 | F2G2 | F2G2 | K4 | F2G2 | F2G2 | F3G3 | F1G1 | F3G1 | F1G1 | F1 | F3G2 | F2 | Increased tillers, fruit set |
| 3813 | 0 | F1 | F2 | 0 | 0 | F1 | 0 | F2 | 0 | F1 | F2 | 0 | |
| 3814 | F3G3 | K4 | K4 | F3G2 | F3G3 | F3G3 | F2G2 | F3G3 | F2G2 | F3G2 | F3G3 | F3G1 | Increased tillers, fruit set |
| 3815 | K4 | K4 | K4 | F3G3 | F3G3 | K4 | G1 | F3G2 | F1G1 | F1 | F3G1 | F2 | Increased fruit set |
| 3816 | 0 | — | F2G1 | 0 | 0 | 0 | 0 | F1 | 0 | 0 | 0 | 0 | |
| 3849 | F2G2 | F3G2 | F3G3 | F1G2 | F2G2 | F2G2 | F2G2 | F3G3 | F2G2 | F2G2 | F3G3 | F3G1 | Increased fruit set, tillers |
| 3850 | 0 | F1G1 | F3G1 | G1 | 0 | F1 | F1 | F3 | F1 | F1 | F2G1 | F3 | Increased fruit set |
| 3851 | 0 | 0 | 0 | 0 | 0 | 0 | 0 | F1 | 0 | 0 | F1 | F1 | |
| 3977 | 0 | F1 | F2G1 | 0 | F1 | F2 | 0 | F2 | N2G2 | F1 | F3 | F3 | |
| 4017 | 0 | 0 | 0 | 0 | 0 | 0 | 0 | F2 | 0 | 0 | F1 | F1 | |
| 4019 | 0 | 0 | 0 | 0 | 0 | 0 | 0 | F1 | 0 | 0 | F1 | F1 | Increases fruit set |
| 4020 | 0 | F1 | 0 | 0 | 0 | F1 | 0 | 0 | 0 | 0 | F1 | F1 | Increases fruit set |
| 4021 | 0 | — | 0 | N1 | 0 | N1 | 0 | 0 | 0 | 0 | 0 | 0 | |
| 4023 | F1 | F2G2 | F2G1 | F1G1 | F2G2 | F3G2 | F1 | F2G1 | F2G1 | F2G1 | F3G1 | F2 | Increases fruit set, tillers |
| 4025 | 0 | F1 | F2 | 0 | 0 | F1 | F1G1 | F2G1 | F1 | F1 | F2G2 | F1 | Increases fruit set, tillers |
| 4026 | 0 | F1 | F2 | 0 | 0 | G2F2 | F1 | F2 | F1 | F2 | F1 | F2 | |
| 4027 | F2G2 | N4 | N4 | F2G2 | F2G1 | F3G1 | F2G1 | F2G1 | F2G1 | F1G1 | F3G2 | F3E1 | Increased fruit set, elongated growth |

TABLE I-continued

| | | | | | | | | | | | | | |
|---|---|---|---|---|---|---|---|---|---|---|---|---|---|
| 4028 | 0 | 0 | F2 | 0 | F1 | F2 | F1 | F3G1 | F1 | F2 | F2G1 | F1 | |
| 4029 | 0 | 0 | F1 | 0 | 0 | F1 | 0 | 0 | 0 | 0 | 0 | 0 | |
| 4030 | F1G1 | F2G2 | F3G3 | F1G1 | F3G3 | F3G3 | F2G1 | F3G1 | F2G2 | F3G2 | F3G2 | F3G1 | Increased fruit set, tillers |
| 4033 | 0 | 0 | 0 | 0 | 0 | 0 | 0 | F1 | 0 | 0 | F1 | F1 | Increased fruit set |
| 4034 | 0 | 0 | 0 | 0 | 0 | 0 | 0 | 0 | 0 | 0 | F1 | F1 | |
| 4035 | 0 | 0 | 0 | 0 | 0 | F1 | 0 | F1 | 0 | 0 | F1 | F1 | Increased fruit set |
| 4036 | 0 | 0 | 0 | 0 | 0 | 0 | 0 | 0 | 0 | 0 | N2F1 | F1 | |
| 4062 | F2G2 | F3G2 | F3G3 | F3G2 | F3G2 | F3G3 | F1 | F3G2 | F1 | F3G2 | F2G1 | F3E1 | Increased fruit set, elongated growth |
| 4063 | F3G3 | F3G2 | K4 | F3G3 | F3G3 | F3G2 | F2G2 | F3G2 | F2G1 | F2G2 | F3G3 | F3G1 | Increased fruit set and tillers |
| 4064 | F3G3 | N4 | F3G2 | F2G1 | F2G1 | F2G1 | F1G1 | F3G2 | F1G1 | F2G2 | F3G2 | F3G1 | Fruit set, tillers |
| 4065 | 0 | 0 | 0 | 0 | 0 | 0 | 0 | F1 | 0 | 0 | 0 | 0 | |
| 4066 | 0 | F1 | F2 | F1 | F1 | F2G1 | 0 | F1 | 0 | 0 | F1 | 0 | More fruit set |
| 4068 | F2G2 | F1G1 | F2 | F1G1 | G1 | F1G1 | 0 | F2 | F1 | F1 | F1 | F3 | Fruit set tillers |
| 4070 | F1G1 | 0 | F1 | 0 | 0 | F1 | 0 | F1 | 0 | 0 | F1 | F1 | Fruit set |
| 4115 | F1G1 | F1 | F2 | F2G1 | F2G2 | F3G1 | F1 | F1 | F1 | F1 | F1 | F2 | Fruit set |
| 4116 | 0 | 0 | 0 | 0 | 0 | F1 | 0 | 0 | 0 | F1 | F1 | F1 | Fruit set |
| 4117 | F2G1 | F2 | F2G1 | F2G2 | F2G2 | F2G1 | F1G1 | F2G2 | F1 | F2G1 | N4 | F3 | |
| 4118 | F2G2 | F2G1 | F3G2 | F3G2 | F2G2 | F2G2 | F2G2 | F2G1 | F2G1 | F2 | F2G1 | F3 | Fruit set, tillers |
| 4119 | G1 | F1 | F1 | 0 | F1 | F1 | F1G1 | F3G2 | F2G1 | F2 | F3G2 | F3G1 | Fruit set, tillers |
| 4120 | F1G1 | F1 | F3G1 | F2G1 | F2G1 | F3G2 | F2G1 | F3G2 | F2G1 | F2G2 | F3G2 | F3 | Fruit set, tillers |
| 4121 | 0 | F1 | F1G1 | 0 | F1 | F2G1 | F1 | F2 | F1G1 | F1 | F2 | F2 | Inc. fruit set, tillers |
| 4122 | G1 | F1 | F2G1 | 0 | 0 | F2G1 | F1G1 | F3G2 | F1G1 | F1 | F2 | F3G1 | Tillers |
| 4123 | 0 | 0 | 0 | 0 | 0 | 0 | 0 | 0 | 0 | 0 | F1 | 0 | |
| 4124 | 0 | 0 | F1 | 0 | 0 | F1 | 0 | F1 | F1 | F1 | F1 | F1 | Good fruit set |
| 4125 | 0 | 0 | 0 | 0 | 0 | 0 | 0 | F1 | F1 | 0 | F1 | F1 | Fruit set |
| 4126 | F1 | F2 | F3G1 | F2G1 | F2G1 | F3G2 | F1G1 | F3G1 | F2G1 | F2G2 | F1G1 | F3G3 | Dark green, tillers |
| 4127 | F2G2 | F3G2 | F3G3 | F3G2 | F3G3 | F2G1 | F2G2 | F3G2 | F2G1 | F1G1 | F2G1 | F3G1 | Fruit set, tillers |
| 4128 | F1G1 | F2G1 | F3G2 | F3G2 | F2G2 | F2G1 | F1G1 | F2G1 | F1 | F2G2 | F2G1 | F3 | Fruit set |
| 4129 | F2G1 | F3G3 | F3G3 | F2G1 | F2G2 | F2G2 | F1 | F2 | 0 | F1 | F2 | F3 | Fruit set |
| 4130 | F2G2 | F3G2 | F3G3 | F3G2 | F3G3 | F3G3 | F2G2 | F2G1 | F1 | F2G1 | F2G2 | F3 | Fruit set |
| 4259 | 0 | 0 | F1 | 0 | 0 | 0 | F1G1 | F2G1 | F1 | F1G1 | F2 | F3G1 | Fruit set |
| 4261 | 0 | 0 | 0 | 0 | 0 | 0 | 0 | 0 | 0 | 0 | F1 | 0 | |
| 4262 | 0 | F1 | F2 | F1G1 | F2 | F2 | 0 | F1 | 0 | F1G1 | F2G1 | F3 | Fruit set |
| 4263 | 0 | 0 | 0 | 0 | 0 | 0 | 0 | — | 0 | F1 | 0 | | |
| 4264 | 0 | F1 | F3 | F1 | F1 | F2 | F1G1 | F2G1 | F1 | F1G1 | F3G1 | F3G1 | Fruit set |
| 4290 | F3G2 | F2G2 | F3G3 | F3G2 | F2G2 | F3G2 | F2G1 | F3G2 | — | F2G2 GW2 | F3G3 | F3G3 | Fruit set |
| 4291 | F3G3 | F3G3 | F3G2 | F3G3 | K4 | K4 | F3G3 | F3G3 | — | F3G3 | F3G3 | F3E3 | |
| 4292 | 0 | F1 | F1 | F1 | 0 | 0 | F1 | F3G2 | F1 | F1 | F2G2 | F3 | |
| 4293 | 0 | 0 | F1 | 0 | 0 | 0 | F1 | 0 | F1 | 0 | F1 | 0 | |
| 4329 | F2G1 | K4 | F2G1 | F1G1 | F1 | F3G1 | N2G1 | F3G2 | F1 | F1 | F2 | F3 | |
| 4330 | F3G2 | F2 | F3G1 | F3G2 | F2G1 | F3G1 | F1G1 | F2 | F1 | F1 | F2 | F3 | Fruit set |
| 4331 | F2G2 | F1 | F3G1 | F2G1 | F1 | F2G1 | N1G1 | F1 | F1 | F1 | F2 | F2 | Fruit set |
| 4332 | F3G2 | F2G1 | F3G2 | F3G2 | F3G3 | F3G3 | F2G2 | F3G3 | F2G1 | F2 | F3G2 | F3 | Fruit set oat tillers |
| 4333 | F2G1 | F2 | F3G1 | F2G1 | F1 | F2G1 | F1G1 | F3G2 | F1 | F2 | F2G1 | F1 | Tillers |
| 4355 | F3G3 | F3G3 | F3G3 | F3G2 | F3G2 | F3G3 | N2G2 | F3G3 | F1 | N1G1 | N4 | F2N1 | Tillers |
| 4373 | F1 | F2G2 | F2 | F1 | 0 | F2G1 | 0 | F1 | F1 | F1 | F1G1 | F2 | Fruit set tillers |
| 4374 | G1 | G1 | 0 | 0 | 0 | F2 | 0 | F1 | 0 G1 | F1 | F1 | Fruit set | |
| 4375 | 0 | F2 | F1 | F1 | F1G1 | F2G1 | N1 | F2 | 0 | N2F1 | F3G2 | F2 | Fruit set |
| 4429 | 0 | F1 | 0 | F1 | F2 | F2 | | | | | | | Fruit set |
| 4230 | 0 | 0 | 0 | 0 | 0 | 0 | 0 | 0 | 0 | 0 | 0 | F1 | |
| 4496 | 0 | F1 | 0 | 0 | 0 | F1 | N1 | F1 | 0 | N1 | F1 | F1 | |
| 4497 | 0 | 0 | 0 | 0 | 0 | 0 | 0 | F3G2 | F1 | F1 | F2G1 | F1 | |
| 4498 | 0 | 0 | 0 | 0 | 0 | 0 | 0 | 0 | 0 | F1 | F1 | F1 | |
| 4499 | 0 | 0 | 0 | 0 | 0 | 0 | N1F1 | F3G2 | F1 | F1 | F1 | F1 | |
| 4500 | 0 | 0 | 0 | 0 | 0 | 0 | 0 | 0 | 0 | 0 | F1 | F2 | |
| 4501 | 0 | 0 | F1 | 0 | 0 | 0 | F1 | F3G2 | F1 | F1 | F2G1 | F2 | Increased fruit set |
| 4502 | F2G2 | F2G2 | F3G2 | F3G2 | F2G2 | F1G1 | F2G1 | F3G3 | F2 | F2 | F2G1 | F3 | Increased fruit set |
| 4503 | K4 | F3G3 | K4 | F3G3 | F3G3 | K4 | F3G2 | F3G3 | F2G1 | F3G3 | F3G2 | F3 | Increased fruit set |
| 4504 | K4 | K4 | F3G3 | F3G3 | F3G3 | F3G3 | F2G2 | F3G3 | F2G1 | F2G2 | F2G1 | F3 | Increased fruit set |
| 4505 | F3G3 | K4 | F3G3 | F3G3 | F3G2 | F3G2 | F2G2 | F3G3 | F2G1 | F2G1 | F3G1 | F3 | Increased fruit set |
| 4455 | 0 | F1 | 0 | F1 | F1 | 0 | | | | | | | |
| 4456 | 0 | F2G2 | 0 | F1 | F1 | F1 | | | | | | | |
| 4457 | F2G1 | F3G2 | F2 | F2 | F2G1 | F3 | | | | | | | Tillers |

TABLE I-continued

| | | | | | | | | | | | | |
|---|---|---|---|---|---|---|---|---|---|---|---|---|
| 4458 | F2G1 | F3G3 | F2 | F1 | F2 | F3 | | | | | | Tillers |
| 4459 | 0 | F1 | 0 | F1 | F2 | F1 | | | | | | |
| 4460 | N1G1 | F2G1 | 0 | F1 | F1 | 0 | | | | | | |
| 4461 | N2G2 | F3G3 | F2 | F3G2 | F3G2 | F3G1 | | | | | | Fruit set, tillers |
| 4462 | N1G1 | F3G3 | F2 | F2 | F3G2 | F2 | | | | | | Fruit set, tillers |
| 4463 | N1G1 | F3G3 | F2G1 | F2G1 | F3G2 | F3G1 | | | | | | Fruit set, tillers |
| 4313 | F1G1 | G1 | 0 | F1G1 | 0 | F2G1 | 0 | 0 | 0 | 0 | F1 | 0 |
| 4359 | F1 | — | F2 | F2G2 | F1 | F3G1 | 0 | F1G1 | 0 | F1G1 | F1G1 | F1 | Fruit set |
| 4360 | 0 | F1 | F1 | F2G1 | 0 | F1 | 0 | F1 | 0 | F1 | F1 | F1 | Fruit set |

EFFECTS ON PLANT SPECIES
of Compounds of the formula

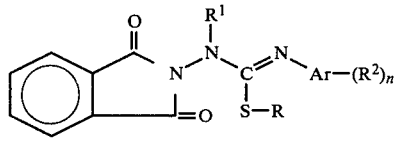

| Com- | Preemergent Effects | | | | | | Postemergent Effects | | | | | | |
|---|---|---|---|---|---|---|---|---|---|---|---|---|---|
| pound No. | Crab- grass | Cox- comb | Brome | Millet | Radish | Sugar Beet | Millet | Al- falfa | Oat | Radish | Sugar Beet | Toma- to | Comments on Utility |
| 4258 | 0 | 0 | F1 | 0 | 0 | 0 | F1G1 | F2G1 | F1 | F1G1 | F2 | F3G1 | Increased fruit set |

The use of many of the growth regulator compounds may be demonstrated by treatment of soybeans (*Soja max*) to increase the number of seed pods and by treating tomato plants (*Lycopersicum esculentum*) to increase fruit set. In an illustrative experiment, Soja max (Evans variety) and Lycopersicum esculentum (Tiny Tim variety) were grown in 4-inch pots (one plant per pot) filled with greenhouse potting soil (2 parts good top soil, 1½ parts builder's sand, 1½ parts peat, fertilized with 5 lb. of 12-12-6 fertilizer and 5 lb. of finely ground limestone per cu. yd.). Aqueous spray formulations were prepared and the potted plants were sprayed at a spray volume of 40 gal. per acre and at application rates of 16, 4, 1 and ¼ oz. per acre. The spray mixtures were prepared by dissolving the proper amount of growth regulator compound in 15 ml. of acetone, adding 2 ml. of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 80 ml by addition of a 0.156 wt. percent aqueous solution of liquid non-ionic dispersant (90 wt. percent active trimethylnonyl polyethylene glycol ether, Tergitol TMN-10). Two replicates were sprayed at all application rates. For comparative purposes, plants were also sprayed at 40 gal./acre with water. The number of seed pods and of fruit as percentage of arithmetic mean of the numbers on untreated plants was observed within approximately three weeks after spray treatment and the results are tabulated below. The extent of growth regulatory effect on the plants was estimated on a scale of 0 to 10 and is also recorded in the following table:

GROWTH REGULATING EFFECTS ON TWO SPECIES

| Compound No. | Rate oz/ A | Soja max | | Lycopersicum esculentum | |
|---|---|---|---|---|---|
| | | Pod Count[1] Percent in Comparison to Untreated Plants | Severity of Growth Regulating Effect[2] | Fruit Count Percent in Comparison to Untreated Plants | Severity of Growth Regulating Effect[2] |
| 2878 | 16 | 163 a,c | 9 | 73 a,b | 9 |
| | 4 | 183 a,c | 6.5 | 364 a,b | 9 |
| | 1 | 117 | 3 | 327 | 4 |
| 2960 | 16 | 160 a,c | 9 | 218 a | 9 |
| | 4 | 138 | 6.5 | 218 e | 7 |
| | 1 | 135 | 6.5 | 327 | 2 |
| 3099 | 16 | 183 a,c | 9 | 182 b | 9 |
| | 4 | 177 a,c | 6.5 | 400 b | 8 |
| | 1 | 186 | 2.5 | 436 b | 4.5 |
| 3100 | 16 | 166 a,c | 9 | 82 a | 9 |
| | 4 | 166 | 6.5 | 382 e | 6.5 |
| | 1 | 146 | 4 | 355 | 4 |
| 3105 | 16 | 185 a,c | 9 | 136 | 9 |
| | 4 | 171 | 7 | 382 | 6.5 |
| | 1 | 143 | 4 | 355 | 3 |
| 3143 | 16 | 166 a,c | 9 | 245 a | 9 |
| | 4 | 169 | 6 | 191 d | 7.5 |
| | 1 | 157 | 2 | 191 e | 3.5 |
| 3144 | 16 | 199 a,c | 9 | 55 a | 9 |
| | 4 | 157 | 5.5 | 382 d | 7 |
| | 1 | 157 | 2.5 | 245 e | 5 |
| 3176 | 16 | 111 | 2 | 178 b | 7.5 |
| | 4 | 104 | 0 | 141 | 3 |
| | 1 | 93 | 0 | 131 | 1 |
| 3251 | 16 | 86 | 0 | 129 | 0.5 |
| | 4 | 95 | 0 | 64 | 0 |
| | 1 | 91 | 0 | 64 | 0 |
| 3274 | 16 | 114 | 0.5 | 107 | 0 |
| | 4 | 105 | 1 | 150 | 0 |
| | 1 | 86 | 0 | 86 | 0 |
| 3277 | 16 | 146 | 6.5 | 197 b | 8.5 |
| | 4 | 143 | 4.5 | 169 | 5.5 |
| | 1 | 154 | 2 | 122 | 1.5 |
| 3278 | 16 | 95 | 0 | 150 | 0.5 |
| | 4 | 91 | 0 | 107 | 0 |
| | 1 | 100 | 0 | 64 | 0 |
| 3293 | 16 | 154 | 7.5 | 141 b | 8 |
| | 4 | 150 | 3.5 | 178 | 4.5 |
| | 1 | 121 | 1 | 113 | 2.5 |
| 3294 | 16 | 154 a | 7.5 | 197 d | 7.5 |
| | 4 | 121 c | 4.5 | 169 b | 3.5 |
| | 1 | 154 | 1.5 | 122 | 2.5 |
| 3295 | 16 | 136 | 8 | 216 | 8 |
| | 4 | 175 | 4 | 188 | 3 |
| | 1 | 145 | 2 | 169 | 1.5 |
| 3297 | 16 | 139 | 1 | 113 | 0.5 |
| | 4 | 132 | 0 | 122 | 0 |

GROWTH REGULATING EFFECTS ON TWO SPECIES

| Compound No. | Rate oz/A | Soja max Pod Count[1] Percent in Comparison to Untreated Plants | Soja max Severity of Growth Regulating Effect[2] | Lycopersicum esculentum Fruit Count Percent in Comparison to Untreated Plants | Lycopersicum esculentum Severity of Growth Regulating Effect[2] |
|---|---|---|---|---|---|
| | 1 | 114 | 0 | 84 | 0 |
| 3298 | 16 | 107 | 0.5 | 113 | 2 |
| | 4 | 118 | 0 | 141 | 0.5 |
| | 1 | 107 | 0 | 103 | 0 |
| 3299 | 16 | 118 | 1 | 279 | 2 |
| | 4 | 109 | 0.5 | 64 | 0 |
| | 1 | 86 | 0 | 21 | 0 |
| 3300 | 16 | 109 | 1 | 86 | 0 |
| | 4 | 114 | 0 | 129 | 0 |
| | 1 | 86 | 0 | 107 | 0 |
| 3302 | 16 | 86 | 1.5 | 107 | 1.5 |
| | 4 | 127 | 0.5 | 107 | 0 |
| | 1 | 118 | 0 | 86 | 0 |
| 3303 | 16 | 118 | 1.5 | 193 | 0.5 |
| | 4 | 123 | 1 | 43 | 0 |
| | 1 | 123 | 0 | 107 | 0 |
| 3339 | 16 | 107 | 0 | 94 | 0 |
| | 4 | 111 | 0 | 131 | 0 |
| | 1 | 114 | 0 | 103 | 0 |
| 3340 | 16 | 105 | 0 | 150 | 0 |
| | 4 | 105 | 0 | 171 | 0 |
| | 1 | 114 | 0 | 193 | 0 |
| 3342 | 16 | 140 | 3 | 400 | 0 |
| | 4 | 105 | 0.5 | 200 | 0 |
| | 1 | 94 | 0 | 0 | 0 |
| 3344 | 16 | 136 c | 6 | 364 | 4 |
| | 4 | 145 | 3 | 321 | 2.5 |
| | 1 | 114 | 1.5 | 300 | 2 |
| 3345 | 16 | 143 | 5 | 169 b | 4.5 |
| | 4 | 164 | 3.5 | 188 | 2.5 |
| | 1 | — | 1 | 159 | 1 |
| 3346 | 16 | 159 a | 7 | 300 a | 8.5 |
| | 4 | 141 c | 5 | 279 b | 8 |
| | 1 | 123 | 2.5 | 364 | 4.5 |
| 3410 | 16 | 114 a[1] | 7.5 | 407 a,d | 8 |
| | 4 | 141 c[1] | 5.5 | 343 b,d | 7.5 |
| | 1 | 105 [1] | 3 | 321 | 5 |
| 3497 | 16 | 121 | 0.5 | 141 | 1 |
| | 4 | 111 | 0 | 103 | 0 |
| | 1 | 111 | 0 | 122 | 0 |
| 3627 | 16 | 121 | 4.5 | 159 | 2 |
| | 4 | 104 | 2.5 | 141 | 2.5 |
| | 1 | 100 | 1 | 141 | 1.5 |
| 3628 | 16 | 125 a | 6.5 | 159 b | 8 |
| | 4 | 150 c | 6 | 188 d | 7.5 |
| | 1 | 136 | 2.5 | 169 | 3.5 |
| 3631 | 16 | 129 | 1.5 | 122 | 0.5 |
| | 4 | 104 | 0 | 84 | 0 |
| | 1 | 107 | 0 | 103 | 0 |
| 3632 | 16 | 132 a | 7.5 | 178 b | 7.5 |
| | 4 | 146 | 4.5 | 216 d | 6 |
| | 1 | 143 | 2.5 | 169 | 4.5 |
| 3633 | 16 | 143 | 2.5 | 700 | 3 |
| | 4 | 129 | 0.5 | 400 | 0.5 |
| | 1 | 112 | 0 | 0 | 0 |
| 3637 | 16 | 127 | 1.5 | 107 | 0 |
| | 4 | 136 | 0 | 129 | 0 |
| | 1 | 95 | 0 | 86 | 0 |
| 3700 | 16 | 143 | 4 | 159 | 4.5 |
| | 4 | 121 | 2.5 | 150 | 3.5 |
| | 1 | 104 | 0 | 141 | 1 |
| 3706 | 16 | 105 | 0.5 | 21 | 0 |
| | 4 | 109 | 0 | 64 | 0 |
| | 1 | 82 | 0 | 86 | 0 |
| 3707 | 16 | 123 | 2 | 300 | 3 |
| | 4 | 150 | 1 | 150 | 1 |
| | 1 | 136 | 0 | 129 | 0 |
| 3709 | 16 | 109 c | 5.5 | 300 | 2.5 |
| | 4 | 145 | 4 | 364 | 1 |
| | 1 | 114 | 0.5 | 321 | 0.5 |
| 3710 | 16 | 167 a | 8.5 | 900 a | 8 |
| | 4 | 136 c | 5 | 700 b | 5.5 |
| | 1 | 143 | 3.5 | 700 | 4.5 |
| 3751 | 16 | 90 | 0 | 75 | 0 |
| | 4 | 93 | 0 | 300 | 0 |
| | 1 | 93 | 0 | 75 | 0 |
| 3752 | 16 | 183 | 8 | 225 | 9 |
| | 4 | 153 | 4.5 | 600 | 8.5 |
| | 1 | 161 | 2.5 | 975 | 5 |
| 3789 | 16 | 93 | 0.5 | 75 | 0.5 |
| | 4 | 117 | 0 | 75 | 0 |
| | 1 | 93 | 0 | 150 | 0 |
| 3792 | 16 | 145 | 8 | 525 | 9 |
| | 4 | 123 | 4 | 1050 | 7 |
| | 1 | 117 | 2 | 675 | 4.5 |
| 3812 | 16 | 106 | 3 | 392[1,2] | 1.5 |
| | 4 | 95 | 1 | 485[2] | 1.5 |
| | 1 | 106 | 0 | 369[2] | 1 |
| 3849 | 16 | 166 a | 7.5 | 254 d | 8.5 |
| | 4 | 166 c | 5 | 692 b | 6 |
| | 1 | 127 | 3 | 438 | 4.5 |
| 3850 | 16 | 113 | 2 | 277 | 3 |
| | 4 | 113 | 0 | 485 | 2.5 |
| | 1 | 120 | 0 | 369 | 1 |
| 3952 | 16 | 82 | 2 | 129 | 0 |
| | 4 | 105 | 0.5 | 129 | 0 |
| | 1 | 105 | 0 | 64 | 0 |
| 3977 | 16 | 137 | 5 | 1000 | 7 |
| | 4 | 119 | 1.5 | 550 | 2.5 |
| | 1 | 112 | 0 | 250 | 1 |
| 4062 | 16 | 133 a | 7 | 236 b | 4 |
| | 4 | 142 c | 5 | 139 | 1.5 |
| | 1 | 146 | 2.5 | 161 | 1.5 |
| 4120 | 16 | 100 a | 4.5 | 214 | 4.5 |
| | 4 | 142 c | 2.5 | 139 | 4 |
| | 1 | 117 | 1 | 129 | 2 |
| 4121 | 16 | 158 | 3 | 129 | 1 |
| | 4 | 142 | 0.5 | 107 | 0.5 |
| | 1 | 121 | 0 | 86 | 0 |
| 4122 | 16 | 125 | 5 | 96 | 1.5 |
| | 4 | 117 | 2.5 | 96 | 1 |
| | 1 | 96 | 0.5 | 139 | 0 |
| 4123 | 16 | 104 | 0 | 139 | 0.5 |
| | 4 | 100 | 0 | 118 | 0 |
| | 1 | 113 | 0 | 150 | 0 |
| 4124 | 16 | 121 | 4.5 | 139 | 1 |
| | 4 | 113 | 0.5 | 129 | 0 |
| | 1 | 104 | 0 | 139 | 0 |
| 4125 | 16 | 113 | 1.5 | 129 | 0.5 |
| | 4 | 113 | 0 | 161 | 0.5 |
| | 1 | 88 | 0 | 107 | 0 |

[1] Check = 100
[2] Greenhouse rating on scale of 0, no effect to 10, total kill.
[a] injury
[b] malformed fruit
[c] smaller pods
[d] increased growth
[e] pear-shaped fruit The information presented in tabular form herein will enable a worker in the art to make a selection from among the growth regulant compounds of the invention and to make some judgment with regard to application rates, depending upon the effect which is desired. It may be seen, for example, that total kills of some species of vegetation may occur at application rates as high as 5 to 10 lb. per acre, whereas beneficial effects may be observed on living plants at application rates of 1 lb. per acre or less.

The growth regulant compounds are usually applied in combination with inert carriers or diluents, as in aqueous sprays, granules and dust formulations in accordance with established practice in the art. An aqueous spray is usually prepared by mixing a wettable powder or emulsifiable concentrate formulation of a growth regulant with a relatively large amount of water to form a dispersion.

Wettable powders comprise intimate, finely divided mixtures of growth regulant compounds, inert solid carriers and surface active agents. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to about 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensation of ethylene oxide with alkylphenols.

Emulsifiable concentrates of the growth regulant compounds comprise in each instance, a solution of growth regulant compound in a liquid carrier which is a mixture of water-immiscible solvent and surfactants, including emulsifiers. Useful solvents include aromatic hydrocarbon solvents such as the xylenes, alkylnaphthalenes, petroleum distillates, terpene solvents, ether-alcohols and organic ester solvents. Suitable emulsifiers, dispersing and wetting agents may be selected from the same classes of products which are employed in formulating wettable powders.

Usually, the growth regulators are applied by diluting with water agricultural compositions which desirably contain from 0.1 percent to 95 percent by weight of active compound and from 0.1 to 75 percent of a carrier or surfactant. However, direct application to plant seeds prior to planting may be accomplished in some instances by mixing powdered solid growth regulator with seed to obtain a substantially uniform coating which is very thin and comprises only one or two percent by weight or less, based on the weight of the seed. In most instances, however, a nonphytotoxic solvents, such as methanol is employed as a carrier to facilitate the uniform distribution of growth regulator on the surface of the seed.

When a compound is to be applied to the soil, as for a pre-emergence application, granular formulations are sometimes more convenient than sprays. A typical granular formation comprises the growth regulator compound dispersed on an inert carrier such as coarsely ground clay, or clay which has been converted to granules by treatment of a rolling bed of the powdered material with a small amount of liquid in a granulating drum. In the usual process for preparing granular formulations, a solution of the active compound is sprayed on the granules while they are being agitated in a suitable mixing apparatus, after which the granules are dried with a current of air during continued agitation.

We claim:

1. The method of regulating the growth of plants comprising applying to the plants, the seed or the soil an effective amount of a compound which has the structural formula:

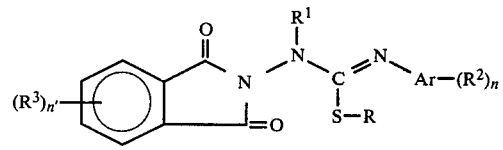

In which R is cyano, $C_1$ to $C_4$ alkyl, $C_3$ to $C_5$ alkenyl or fluoroalkenyl, propynyl, phenylallyl or $C_1$ to $C_3$ alkyl to which is attached a phenyl, bromophenyl, chlorophenyl, methylphenyl, pyridyl, benzoyl, trimethylacetyl, phenoxy, chlorophenoxy, methylthio, fluorobenzoyl, N-phenylcarbamyl, N-ethylcarbamyl, N-trifluoromethylthiadiazolylcarbamyl, carboxy or carbethoxy substituent, $R^1$ is H, acetyl, $C_1$ to $C_3$ alkyl, alkenyl or alkynyl to which may be attached phenyl, halophenyl, carbethoxy, vinyloxy or phenoxy groups, or R and $R^1$ together may be $C_2$ to $C_4$ alkylene;

Ar is phenyl or benzoyl;

$R^2$ is $C_1$ to $C_4$ alkyl, alkoxy, alkylene, alkylamino or alkylthio; phenoxy, benzyloxy, carbalkoxy, acetyl, methylenedioxy, trifluoromethyl, nitro, halo or cyano and n represents the number of points of attachment, which may be zero or an integer from 1 to 4, with the provision that at least one position ortho to the point of attachment of a phenyl ring of the Ar structure to the remainder of the molecule must be unsubstituted;

$R^3$ is lower alkyl or halo and n' may be zero or an integer from 1 to 4.

2. The method of claim 1 in which there is used an effective amount of 2-[1,2-dimethyl-3-(3-fluorophenyl)isothioureido]-1H-isoindole-1,3-(2H)dione.

3. The method of regulating the growth of plants which comprises applying to the plants pre- or post-emergently an effective amount of a composition comprising from 0.1 percent to 95 weight percent of a compound as specified in claim 1 in combination with from 0.1 to 75 weight percent of a carrier or surfactant.

4. The method of increasing fruit set of crop plants which comprises applying to the plant foliage an effective amount of a compound as specified in claim 1 in combination with an inert carrier and a surfactant.

5. The method of claim 4 in which the crop plants are of the species *Lycopersicum esculentum.*

6. The method of claim 4 in which the crop plants are of the species *Soja max.*

* * * * *

UNITED STATES PATENT AND TRADEMARK OFFICE
CERTIFICATE OF CORRECTION

PATENT NO. : 4,292,071   Page 1 of 2

DATED : September 29, 1981

INVENTOR(S) : Joel L. Kirkpatrick, Natu R. Patel, and Jerry L. Rutter

It is certified that error appears in the above-identified patent and that said Letters Patent is hereby corrected as shown below:

On the title page

Abstract, first line after formula, insert --or-- before "$C_1$".

Abstract, second line after formula, insert --each of-- before "which".

Column 2, line 20, "spacies" should be --species--.

Column 9, line 10, Table I should appear as shown below:

| Compnd. No. | R | $R^1$ |
|---|---|---|
| 3141 | $-CH_3$ | $-CH_3$ |
| 3143 | Allyl | $-CH_3$ |
| 3144 | benzyl | $-CH_3$ |
| 3171 | $-CH_2-CH_2-$ | |

Column 14, Table I, Compound No. 4027, under M.P.°C. column, insert -- 105-108 --.

Column 19, Table I, Compound No. "3672" should be --3627--.

Column 22, Table I, Compound No. 3792, under heading "Postemergent Effects", "Sugar Beet" column, "F2G3" should be --F2G2--.

UNITED STATES PATENT AND TRADEMARK OFFICE
CERTIFICATE OF CORRECTION

PATENT NO. : 4,292,071

DATED : September 29, 1981

INVENTOR(S) : Joel L. Kirkpatrick, Natu R. Patel, and Jerry L. Rutter

It is certified that error appears in the above-identified patent and that said Letters Patent is hereby corrected as shown below:

Column 25, last line, Compound No. 2878, under "Soja max", "117" should be --177--.

Column 29, line 43, "solvents" should be --solvent--.

Column 30, line 19, after "methylphenyl," delete "pyridyl".

Column 30, lines 21-22, delete "N-trifluoromethylthiadiazolyl-carbamyl".

Signed and Sealed this

Eighteenth Day of January 1983

[SEAL]

Attest:

Attesting Officer

GERALD J. MOSSINGHOFF

Commissioner of Patents and Trademarks